US008685656B2

(12) United States Patent
Dalmau

(10) Patent No.: US 8,685,656 B2
(45) Date of Patent: Apr. 1, 2014

(54) METHODS FOR DIAGNOSING AND TREATING ENCEPHALITIS OR EPILEPSY

(75) Inventor: Josep Dalmau, Delmar, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/498,355

(22) PCT Filed: Sep. 29, 2010

(86) PCT No.: PCT/US2010/050746
§ 371 (c)(1),
(2), (4) Date: Mar. 27, 2012

(87) PCT Pub. No.: WO2011/041433
PCT Pub. Date: Apr. 7, 2011

(65) Prior Publication Data
US 2012/0213803 A1 Aug. 23, 2012

Related U.S. Application Data

(60) Provisional application No. 61/246,843, filed on Sep. 29, 2009.

(51) Int. Cl.
*G01N 33/567* (2006.01)
*C07K 16/28* (2006.01)

(52) U.S. Cl.
USPC ..... 435/7.1; 436/501; 530/387.7; 530/388.22

(58) Field of Classification Search
None
See application file for complete search history.

(56) References Cited

U.S. PATENT DOCUMENTS

| | | | |
|---|---|---|---|
| 6,010,854 A | 1/2000 | Rogers et al. | |
| 2009/0155261 A1 | 6/2009 | Dalmau et al. | |

OTHER PUBLICATIONS

Lancaster et al., Antibodies to the GAGAB receptor in limbic encephalitis with seizures: case series and characterization of the antigen, 2010, Lancet Neurology 9:67-76 (published online Dec. 3, 2009).*

Ances et al. "Treatment responsive limbic encephalitis identified by neuropil antibodies MRI and PET correlates" Brain 128 1764-1777. 1777, (2005).
Vitaliani et al. "Paraneoplastic encephalitis, psychiatric symptoms, and hypoventilation in ovarian teratoma" Ann Neurol. 58:594-604, (2005).
Gultekin et al. "Paraneoplastic limbic encephalitis: neurological symptoms, immunological findings and tumour association in 50 patients" Brain. ; 123(Pt 7):1481-1494. Jul. 2000.
Caudy et al. "Fragile X-related protein and VIG associate with the RNA interference machinery"Genes & Devel 16:2491-96, (2002).
Nielsen. "Peptide nucleic acids as therapeutic agents" Curr. Opin. Struct Biol. 9:353-57, (1999).
Naz NK et al. "Novel human prostate specific cDNA: molecular cloning, expression, and immunobiology of the recombinant protein" Biochem Biophys Res Commun. 297:1075-84. (2002).
Lancaster et al. "Antibodies to the $GABA_B$ receptor in limbic encephalitis with seizures: case series and characterisation of the antigen" Lancet Neurol. 9:67-76, (2010).
Peltola et al. "Autoantibodies to glutamic acid decarboxylase in patients with therapy resistant epilepsy" Neurology; 55:46-50, (2000).
Palace. "Epilepsy: an autoimmune disease?" J Neurol Neurosurg Psychiatry; 69:711-714, (2000).
Irani et al. "Autoantibody-mediated disorders of the central nervous system" Autoimmunity.41 (1):55-65, (2008).
International Search Report Application No. PCT/US 10/50756 Date of Mailing Nov. 23, 2010.
Errichiello et al., "Autoantibodies to glutamic acid decarboxylase (GAD) in focal and generalized epilepsy: A study on 233 patients", Journal of Neuroimmunology, vol. 211, No. 1-2, 2009, pp. 120-123.
Mazzi et al., "Plasma exchange for anti GAD associates non paraneoplastic limbic encephalitis", Transfusion and Apheresis Science, vol. 39, No. 3, 2008, pp. 229-233.
Mitoma et al., "Dual impairment of GABAA- and GABAB-receptor-mediated synaptic responses by autoantibodies to glutamic acid decarboxylase", Journal of Neurological Sciences, vol. 208, No. 1-2, 2003, pp. 51-56.

* cited by examiner

*Primary Examiner* — John Ulm
(74) *Attorney, Agent, or Firm* — Mark S. Cohen; Pearl Cohen Zedek Latzer Baratz LLP

(57) ABSTRACT

This invention provides methods of diagnosing or determining a cause of an autoimmune encephalitis or an epilepsy in a subject and of diagnosing a tumor in a subject, comprising the step of testing a biological sample of the subject for an antibody to a $GABA_B$ receptor. This invention further provides methods of treating an autoimmune encephalitis or an epilepsy, comprising the steps of detecting an antibody to a $GABA_B$ receptor and treating a tumor associated with the disease.

48 Claims, 8 Drawing Sheets

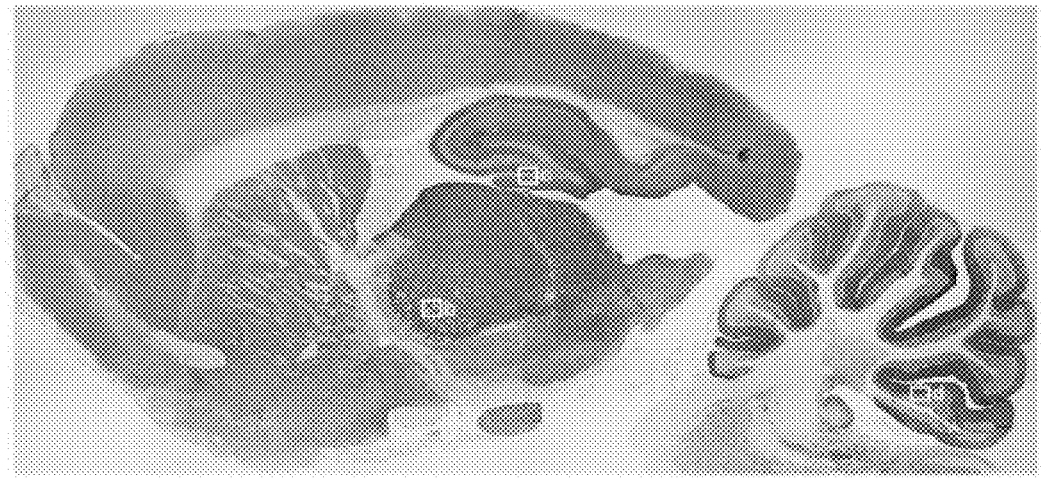
FIGURE 2A
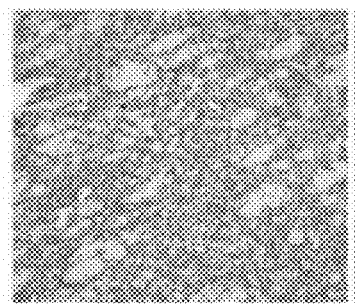 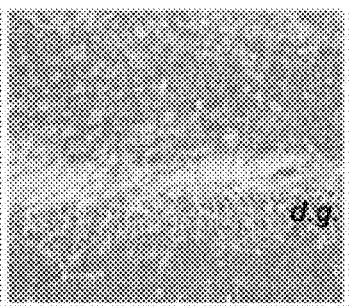 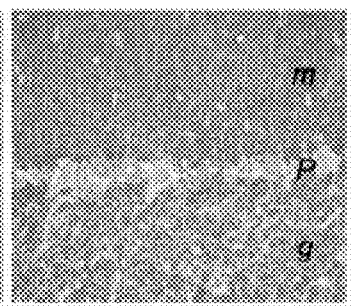
FIGURE 2B　　　FIGURE 2C　　　FIGURE 2D

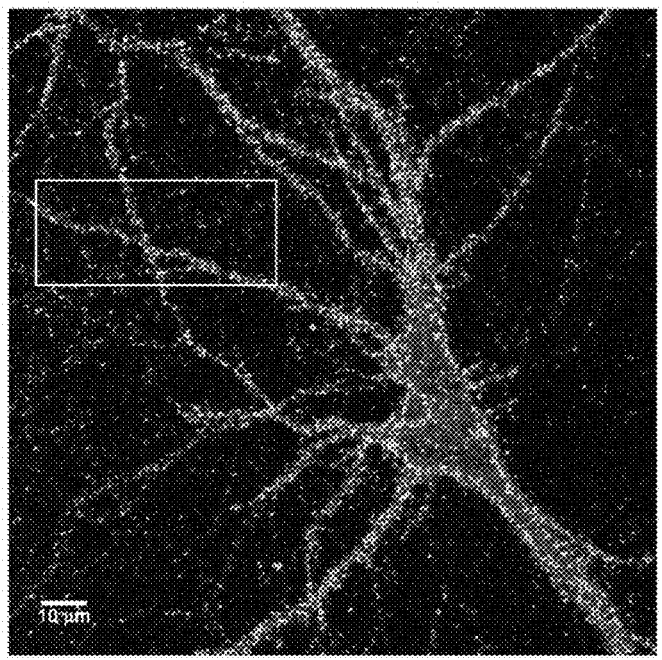
FIGURE 4B
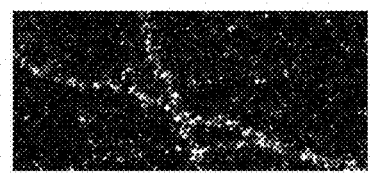
FIGURE 4C
FIGURE 4A
FIGURE 4D
FIGURE 4E
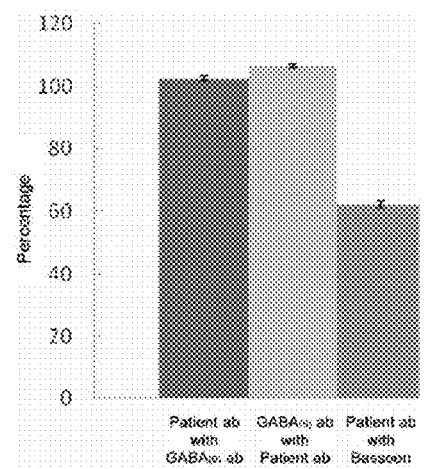
FIGURE 4F

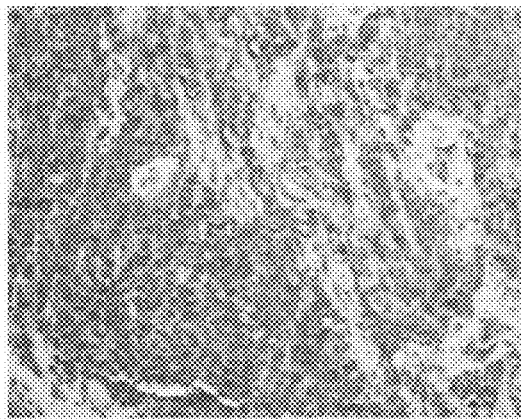
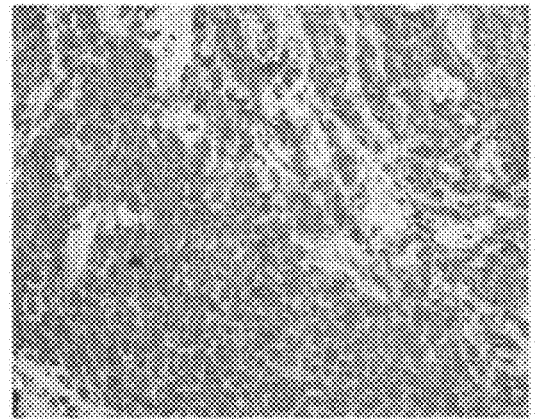
FIGURE 6A                FIGURE 6B
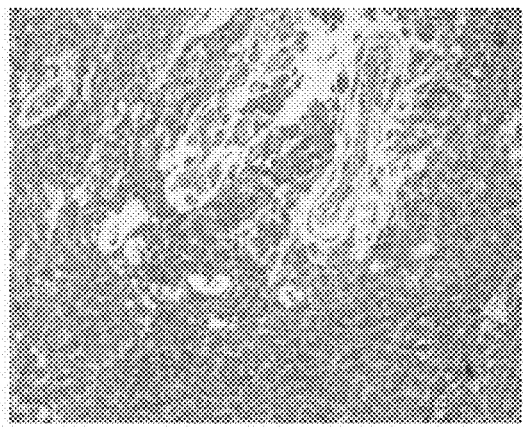
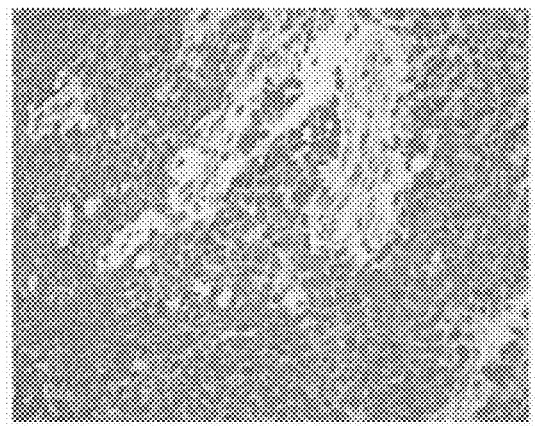
FIGURE 6C                FIGURE 6D

SEQUENCE LISTING

<160> NUMBER OF SEQ ID NOS: 6

<210> SEQ ID NO 1
<211> LENGTH: 961

```
<212> TYPE: PRT
<213> ORGANISM: Homo sapiens

<400> SEQUENCE: 1

Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Ile Arg Tyr Arg Gly Leu Thr Arg
            35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
                100                 105                 110

Phe Leu Thr Gly Gly Asp Leu Pro Ala Leu Asp Gly Ala Arg Val Asp
            115                 120                 125

Phe Arg Cys Asp Pro Asp Phe His Leu Val Gly Ser Ser Arg Ser Ile
130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
            195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
            275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
            355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400
```

```
Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
            435                 440                 445

Lys Leu Thr Lys Arg Leu Lys Arg His Pro Glu Glu Thr Gly Gly Phe
        450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Arg Ser Gly Val Arg Leu Glu
                485                 490                 495

Asp Phe Asn Tyr Asn Asn Gln Thr Ile Thr Asp Gln Ile Tyr Arg Ala
                500                 505                 510

Met Asn Ser Ser Ser Phe Glu Gly Val Ser Gly His Val Val Phe Asp
            515                 520                 525

Ala Ser Gly Ser Arg Met Ala Trp Thr Leu Ile Glu Gln Leu Gln Gly
            530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Gly Ser Pro Pro Ala Asp
                565                 570                 575

Gln Thr Leu Val Ile Lys Thr Phe Arg Phe Leu Ser Gln Lys Leu Phe
            580                 585                 590

Ile Ser Val Ser Val Leu Ser Ser Leu Gly Ile Val Leu Ala Val Val
        595                 600                 605

Cys Leu Ser Phe Asn Ile Tyr Asn Ser His Val Arg Tyr Ile Gln Asn
610                 615                 620

Ser Gln Pro Asn Leu Asn Asn Leu Thr Ala Val Gly Cys Ser Leu Ala
625                 630                 635                 640

Leu Ala Ala Val Phe Pro Leu Gly Leu Asp Gly Tyr His Ile Gly Arg
                645                 650                 655

Asn Gln Phe Pro Phe Val Cys Gln Ala Arg Leu Trp Leu Leu Gly Leu
            660                 665                 670

Gly Phe Ser Leu Gly Tyr Gly Ser Met Phe Thr Lys Ile Trp Trp Val
        675                 680                 685

His Thr Val Phe Thr Lys Lys Glu Lys Lys Glu Trp Arg Lys Thr
        690                 695                 700

Leu Glu Pro Trp Lys Leu Tyr Ala Thr Val Gly Leu Leu Val Gly Met
705                 710                 715                 720

Asp Val Leu Thr Leu Ala Ile Trp Gln Ile Val Asp Pro Leu His Arg
                725                 730                 735

Thr Ile Glu Thr Phe Ala Lys Glu Glu Pro Lys Glu Asp Ile Asp Val
                740                 745                 750

Ser Ile Leu Pro Gln Leu Glu His Cys Ser Ser Arg Lys Met Asn Thr
            755                 760                 765

Trp Leu Gly Ile Phe Tyr Gly Tyr Lys Gly Leu Leu Leu Leu Leu Gly
            770                 775                 780

Ile Phe Leu Ala Tyr Glu Thr Lys Ser Val Ser Thr Glu Lys Ile Asn
785                 790                 795                 800

Asp His Arg Ala Val Gly Met Ala Ile Tyr Asn Val Ala Val Leu Cys
                805                 810                 815

Leu Ile Thr Ala Pro Val Thr Met Ile Leu Ser Ser Gln Gln Asp Ala
            820                 825                 830
```

```
Ala Phe Ala Phe Ala Ser Leu Ala Ile Val Phe Ser Ser Tyr Ile Thr
            835                 840                 845

Leu Val Val Leu Phe Val Pro Lys Met Arg Arg Leu Ile Thr Arg Gly
    850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Glu Arg Val Ser Glu Leu
            900                 905                 910

Arg His Gln Leu Gln Ser Arg Gln Gln Leu Arg Ser Arg Arg His Pro
        915                 920                 925

Pro Thr Pro Pro Glu Pro Ser Gly Gly Leu Pro Arg Gly Pro Pro Glu
    930                 935                 940

Pro Pro Asp Arg Leu Ser Cys Asp Gly Ser Arg Val His Leu Leu Tyr
945                 950                 955                 960

Lys

<210> SEQ ID NO 2
<211> LENGTH: 844
<212> TYPE: PRT
<213> ORGANISM: Homo sapiens

<400> SEQUENCE: 2

Met Gly Pro Gly Ala Pro Phe Ala Arg Val Gly Trp Pro Leu Pro Leu
1               5                   10                  15

Leu Val Val Met Ala Ala Gly Val Ala Pro Val Trp Ala Ser His Ser
            20                  25                  30

Pro His Leu Pro Arg Pro His Ser Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240
```

```
Asp Ala Arg Ile Ile Val Gly Leu Phe Tyr Glu Thr Glu Ala Arg Lys
            245                 250                 255

Val Phe Cys Glu Val Tyr Lys Glu Arg Leu Phe Gly Lys Lys Tyr Val
        260                 265                 270

Trp Phe Leu Ile Gly Trp Tyr Ala Asp Asn Trp Phe Lys Ile Tyr Asp
            275                 280                 285

Pro Ser Ile Asn Cys Thr Val Asp Glu Met Thr Glu Ala Val Glu Gly
        290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Lys Leu Thr Lys Arg
            325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
            355                 360                 365

Gly Gly Gly Arg Ser Gly Val Arg Leu Glu Asp Phe Asn Tyr Asn
        370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
            405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Asp Leu Ser Trp Ser Lys Thr
        435                 440                 445

Asp Lys Trp Ile Gly Gly Ser Pro Pro Ala Asp Gln Thr Leu Val Ile
450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
            485                 490                 495

Ile Tyr Asn Ser His Val Arg Tyr Ile Gln Asn Ser Gln Pro Asn Leu
        500                 505                 510

Asn Asn Leu Thr Ala Val Gly Cys Ser Leu Ala Leu Ala Ala Val Phe
            515                 520                 525

Pro Leu Gly Leu Asp Gly Tyr His Ile Gly Arg Asn Gln Phe Pro Phe
        530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
            565                 570                 575

Lys Lys Glu Glu Lys Lys Glu Trp Arg Lys Thr Leu Glu Pro Trp Lys
            580                 585                 590

Leu Tyr Ala Thr Val Gly Leu Leu Val Gly Met Asp Val Leu Thr Leu
        595                 600                 605

Ala Ile Trp Gln Ile Val Asp Pro Leu His Arg Thr Ile Glu Thr Phe
    610                 615                 620

Ala Lys Glu Glu Pro Lys Glu Asp Ile Asp Val Ser Ile Leu Pro Gln
625                 630                 635                 640

Leu Glu His Cys Ser Ser Arg Lys Met Asn Thr Trp Leu Gly Ile Phe
            645                 650                 655

Tyr Gly Tyr Lys Gly Leu Leu Leu Leu Leu Gly Ile Phe Leu Ala Tyr
        660                 665                 670
```

```
Glu Thr Lys Ser Val Ser Thr Glu Lys Ile Asn Asp His Arg Ala Val
            675                 680                 685

Gly Met Ala Ile Tyr Asn Val Ala Val Leu Cys Leu Ile Thr Ala Pro
        690                 695                 700

Val Thr Met Ile Leu Ser Ser Gln Gln Asp Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
                740                 745                 750

Ala Gln Asp Thr Met Lys Thr Gly Ser Ser Thr Asn Asn Glu Glu
            755                 760                 765

Glu Lys Ser Arg Leu Leu Glu Lys Glu Asn Arg Glu Leu Glu Lys Ile
        770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Pro Thr Pro Pro Glu
                805                 810                 815

Pro Ser Gly Gly Leu Pro Arg Gly Pro Glu Pro Pro Asp Arg Leu
            820                 825                 830

Ser Cys Asp Gly Ser Arg Val His Leu Leu Tyr Lys
        835                 840

<210> SEQ ID NO 3
<211> LENGTH: 899
<212> TYPE: PRT
<213> ORGANISM: Homo sapiens

<400> SEQUENCE: 3

Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Asn Arg Thr Pro His Ser Gly Arg Arg Ala Val Tyr Ile Gly Ala
            100                 105                 110

Leu Phe Pro Met Ser Gly Gly Trp Pro Gly Gly Gln Ala Cys Gln Pro
        115                 120                 125

Ala Val Glu Met Ala Leu Glu Asp Val Asn Ser Arg Arg Asp Ile Leu
    130                 135                 140

Pro Asp Tyr Glu Leu Lys Leu Ile His His Asp Ser Lys Cys Asp Pro
145                 150                 155                 160

Gly Gln Ala Thr Lys Tyr Leu Tyr Glu Leu Leu Tyr Asn Asp Pro Ile
                165                 170                 175

Lys Ile Ile Leu Met Pro Gly Cys Ser Ser Val Ser Thr Leu Val Ala
            180                 185                 190

Glu Ala Ala Arg Met Trp Asn Leu Ile Val Leu Ser Tyr Gly Ser Ser
        195                 200                 205
```

```
Ser Pro Ala Leu Ser Asn Arg Gln Arg Phe Pro Thr Phe Arg Thr
    210                 215                 220
His Pro Ser Ala Thr Leu His Asn Pro Thr Arg Val Lys Leu Phe Glu
225                 230                 235                 240
Lys Trp Gly Trp Lys Lys Ile Ala Thr Ile Gln Gln Thr Thr Glu Val
                245                 250                 255
Phe Thr Ser Thr Leu Asp Asp Leu Glu Glu Arg Val Lys Glu Ala Gly
                260                 265                 270
Ile Glu Ile Thr Phe Arg Gln Ser Phe Phe Ser Asp Pro Ala Val Pro
            275                 280                 285
Val Lys Asn Leu Lys Arg Gln Asp Ala Arg Ile Ile Val Gly Leu Phe
            290                 295                 300
Tyr Glu Thr Glu Ala Arg Lys Val Phe Cys Glu Val Tyr Lys Glu Arg
305                 310                 315                 320
Leu Phe Gly Lys Lys Tyr Val Trp Phe Leu Ile Gly Trp Tyr Ala Asp
                325                 330                 335
Asn Trp Phe Lys Ile Tyr Asp Pro Ser Ile Asn Cys Thr Val Asp Glu
                340                 345                 350
Met Thr Glu Ala Val Glu Gly His Ile Thr Thr Glu Ile Val Met Leu
            355                 360                 365
Asn Pro Ala Asn Thr Arg Ser Ile Ser Asn Met Thr Ser Gln Glu Phe
370                 375                 380
Val Glu Lys Leu Thr Lys Arg Leu Lys Arg His Pro Glu Glu Thr Gly
385                 390                 395                 400
Gly Phe Gln Glu Ala Pro Leu Ala Tyr Asp Ala Ile Trp Ala Leu Ala
                405                 410                 415
Leu Ala Leu Asn Lys Thr Ser Gly Gly Gly Arg Ser Gly Val Arg
                420                 425                 430
Leu Glu Asp Phe Asn Tyr Asn Asn Gln Thr Ile Thr Asp Gln Ile Tyr
            435                 440                 445
Arg Ala Met Asn Ser Ser Phe Glu Gly Val Ser Gly His Val Val
            450                 455                 460
Phe Asp Ala Ser Gly Ser Arg Met Ala Trp Thr Leu Ile Glu Gln Leu
465                 470                 475                 480
Gln Gly Gly Ser Tyr Lys Lys Ile Gly Tyr Tyr Asp Ser Thr Lys Asp
                485                 490                 495
Asp Leu Ser Trp Ser Lys Thr Asp Lys Trp Ile Gly Gly Ser Pro Pro
            500                 505                 510
Ala Asp Gln Thr Leu Val Ile Lys Thr Phe Arg Phe Leu Ser Gln Lys
            515                 520                 525
Leu Phe Ile Ser Val Ser Val Leu Ser Ser Leu Gly Ile Val Leu Ala
            530                 535                 540
Val Val Cys Leu Ser Phe Asn Ile Tyr Asn Ser His Val Arg Tyr Ile
545                 550                 555                 560
Gln Asn Ser Gln Pro Asn Leu Asn Asn Leu Thr Ala Val Gly Cys Ser
                565                 570                 575
Leu Ala Leu Ala Ala Val Phe Pro Leu Gly Leu Asp Gly Tyr His Ile
            580                 585                 590
Gly Arg Asn Gln Phe Pro Phe Val Cys Gln Ala Arg Leu Trp Leu Leu
            595                 600                 605
Gly Leu Gly Phe Ser Leu Gly Tyr Gly Ser Met Phe Thr Lys Ile Trp
            610                 615                 620
Trp Val His Thr Val Phe Thr Lys Lys Glu Glu Lys Lys Glu Trp Arg
```

Lys Thr Leu Glu Pro Trp Lys Leu Tyr Ala Thr Val Gly Leu Leu Val
625                 630                 635                 640

Gly Met Asp Val Leu Thr Leu Ala Ile Trp Gln Ile Val Asp Pro Leu
            645                 650                 655

His Arg Thr Ile Glu Thr Phe Ala Lys Glu Glu Pro Lys Glu Asp Ile
        660                 665                 670

Asp Val Ser Ile Leu Pro Gln Leu Glu His Cys Ser Ser Arg Lys Met
    675                 680                 685

Asn Thr Trp Leu Gly Ile Phe Tyr Gly Tyr Lys Gly Leu Leu Leu Leu
690                 695                 700

Leu Gly Ile Phe Leu Ala Tyr Glu Thr Lys Ser Val Ser Thr Glu Lys
705                 710                 715                 720

Ile Asn Asp His Arg Ala Val Gly Met Ala Ile Tyr Asn Val Ala Val
            725                 730                 735

Leu Cys Leu Ile Thr Ala Pro Val Thr Met Ile Leu Ser Ser Gln Gln
        740                 745                 750

Asp Ala Ala Phe Ala Phe Ala Ser Leu Ala Ile Val Phe Ser Ser Tyr
    755                 760                 765

Ile Thr Leu Val Val Leu Phe Val Pro Lys Met Arg Arg Leu Ile Thr
770                 775                 780

Arg Gly Glu Trp Gln Ser Glu Ala Gln Asp Thr Met Lys Thr Gly Ser
785                 790                 795                 800

Ser Thr Asn Asn Asn Glu Glu Glu Lys Ser Arg Leu Leu Glu Lys Glu
            805                 810                 815

Asn Arg Glu Leu Glu Lys Ile Ile Ala Glu Lys Glu Glu Arg Val Ser
        820                 825                 830

Glu Leu Arg His Gln Leu Gln Ser Arg Gln Gln Leu Arg Ser Arg Arg
    835                 840                 845

His Pro Pro Thr Pro Pro Glu Pro Ser Gly Gly Leu Pro Arg Gly Pro
865                 870                 875                 880

Pro Glu Pro Pro Asp Arg Leu Ser Cys Asp Gly Ser Arg Val His Leu
            885                 890                 895

Leu Tyr Lys

<210> SEQ ID NO 4
<211> LENGTH: 4547
<212> TYPE: DNA
<213> ORGANISM: Homo sapiens

<400> SEQUENCE: 4
ccctctcttc ccccgccct  gccttccctt gcaccctcct tcttccctcc gcccgggagc    60
tctccctggt cccggcgcc  gcctccttcc ctccggctc cccgctcccc gctccgtggg   120
ctgccgccgc ccggggaag  aagagacagg ggtggggttt ggggggaagcg agagaggagg   180 ggagagaccc tggccaggct ggagcctgga ttcgagggga ggagggacgg gaggaggaga    240
aaggtggagg agaagggagg ggggagcggg gaggagcggc cgggcctggg gccttgaggc    300
ccggggagag ccggggagcc gggcccgcgc gccgagatgt tgctgctgct gctactggcg    360
ccactcttcc tccgccccc gggcgcgggc ggggcgcaga cccccaacgc cacctcagaa    420
ggttgccaga tcatacaccc gccctgggaa gggggcatca ggtaccgggg cctgactcgg    480
gaccaggtga aggctatcaa cttcctgcca gtgactatg agattgagta tgtgtgccgg    540 gggggagcgcg aggtggtggg gcccaaggtc cgcaagtgcc tggccaacgg ctcctggaca    600

```
gatatggaca cacccagccg ctgtgtccga atctgctcca agtcttattt gaccctggaa    660
aatgggaagg ttttcctgac gggtggggac ctcccagctc tggacggagc ccgggtggat    720
ttccggtgtg accccgactt ccatctggtg ggcagctccc ggagcatctg tagtcagggc    780
cagtggagca cccccaagcc ccactgccag gtgaatcgaa cgccacactc agaacggcgc    840
gcagtgtaca tcgggcact  gtttcccatg agcgggggct ggccagggg  ccaggcctgc    900 cagcccgcgg tggagatggc gctggaggac gtgaatagcc gcagggacat cctgccggac    960
tatgagctca agctcatcca ccacgacagc aagtgtgatc caggccaagc caccaagtac   1020
ctatatgagc tgctctacaa cgaccctatc aagatcatcc ttatgcctgg ctgcagctct   1080
gtctccacgc tggtggctga ggctgctagg atgtggaacc tcattgtgct ttcctatggc   1140
tccagctcac cagccctgtc aaaccggcag cgtttcccca cttcttccg  aacgcaccca   1200 tcagccacac tccacaaccc tacccgcgtg aaactctttg aaaagtgggg ctggaagaag   1260
attgctacca tccagcagac cactgaggtc ttcacttcga ctctggacga cctggaggaa   1320
cgagtgaagg aggctggaat tgagattact ttccgccaga gtttcttctc agatccagct   1380
gtgcccgtca aaaacctgaa gcgccaggat gcccgaatca tcgtgggact ttttctatgag   1440 actgaagccc ggaaagtttt ttgtgaggtg tacaaggagc gtctctttgg gaagaagtac   1500
gtctggttcc tcattgggtg gtatgctgac aattggttca agatctacga cccttctatc   1560
aactgcacag tggatgagat gactgaggcg gtggagggcc acatcacaac tgagattgtc   1620
atgctgaatc ctgccaatac ccgcagcatt tccaacatga catcccagga atttgtggag   1680
aaactaacca agcgactgaa aagacaccct gaggagacag gaggcttcca ggaggcaccg   1740
ctggcctatg atgccatctg ggccttggca ctggccctga caagacatc  tggaggaggc   1800 ggccgttctg gtgtgcgcct ggaggacttc aactacaaca accagaccat taccgaccaa   1860
atctaccggg caatgaactc ttcgtccttt gagggtgtct ctggccatgt ggtgtttgat   1920
gccagcggct ctcggatggc atggacgctt atcgagcagc ttcagggtgg cagctacaag   1980
aagattggct actatgacag caccaaggat gatctttcct ggtccaaaac agataaatgg   2040
attggagggt ccccccagc  tgaccagacc ctggtcatca agacattccg cttcctgtca   2100
cagaaactct ttatctccgt ctcagttctc tccagcctgg gcattgtcct agctgttgtc   2160
tgtctgtcct ttaacatcta caactcacat gtccgttata tccagaactc acagcccaac   2220
ctgaacaacc tgactgctgt gggctgctca ctggctttag ctgctgtctt ccccctgggg   2280
ctcgatggtt accacattgg gaggaaccag tttcctttcg tctgccaggc ccgcctctgg   2340
ctcctgggcc tgggctttag tctgggctac ggttccatgt tcaccaagat tggtgggtc   2400 cacacggtct tcacaaagaa ggaagaaaag aaggagtgga ggaagactct ggaaccctgg   2460
aagctgtatg ccacagtggg cctgctggtg ggcatggatg tcctcactct cgccatctgg   2520
cagatcgtgg accctctgca ccggaccatt gagacatttg ccaaggagga acctaaggaa   2580
gatattgacg tctctattct gccccagctg gagcattgca gctccaggaa gatgaataca   2640
tggcttggca ttttctatgg ttacaagggg ctgctgctgc tgctgggaat cttccttgct   2700
tatgagacca agagtgtgtc cactgagaag atcaatgatc accgggctgt gggcatggct   2760
atctacaatg tggcagtcct gtgcctcatc actgctcctg tcaccatgat tctgtccagc   2820
cagcaggatg cagcctttgc ctttgcctct cttgccatag ttttctcctc ctatatcact   2880
cttgttgtgc tctttgtgcc caagatgcgc aggctgatca cccgagggga atggcagtcg   2940
gaggcgcagg acaccatgaa gacagggtca tcgaccaaca caacgaggag ggagaagtcc   3000
```

```
cggctgttgg agaaggagaa ccgtgaactg gaaaagatca ttgctgagaa agaggagcgt      3060
gtctctgaac tgcgccatca actccagtct cggcagcagc tccgctcccg gcgccaccca      3120
ccgacacccc cagaaccctc tgggggcctg cccaggggac cccctgagcc ccccgaccgg      3180
cttagctgtg atgggagtcg agtgcatttg ctttataagt gagggtaggg tgagggagga      3240
caggccagta gggggaggga aagggagagg ggaagggcag gggactcagg aagcagggg       3300 tccccatccc cagctgggaa gaacatgcta tccaatctca tctcttgtaa atacatgtcc      3360
ccctgtgagt tctgggctga tttgggtctc tcatacctct gggaaacaga cctttttctc      3420
tcttactgct tcatgtaatt ttgtatcacc tcttcacaat ttagttcgta cctggcttga      3480
agctgctcac tgctcacacg ctgcctcctc agcagcctca ctgcatcttt ctcttcccat      3540
gcaacaccct cttctagtta ccacggcaac ccctgcagct cctctgcctt tgtgctctgt      3600
tcctgtccag caggggtctc ccaacaagtg ctctttccac cccaaggggg cctctccttt      3660
tctccactgt cataatctct ttccatctta cttgcccttc tatactttct cacatgtggc      3720
tccccctgaa ttttgcttcc tttgggagct cattcttttc gccaaggctc acatgctcct      3780
tgcctctgct ctgtgcactc acgctcagca cacatgcatc ctcccctctc ctgcgtgtgc      3840
ccactgaaca tgctcatgtg tacacacgct tttcccgtat gctttcttca tgttcagtca      3900
catgtgctct cgggtgccct gcattcacag ctacgtgtgc ccctctcatg gtcatgggtc      3960
tgcccttgag cgtgtttggg taggcatgtg caatttgtct agcatgctga gtcatgtctt      4020
tcctatttgc acacgtccat gtttatccat gtactttccc tgtgtaccct ccatgtacct      4080
tgtgtacttt cttcccttaa atcatggtat tcttctgaca gagccatatg taccctaccc      4140
tgcacattgt tatgcacttt tccccaattc atgtttggtg gggccatcca cccctctcc      4200 ttgtcacaga atctccattt ctgctcagat tcccccatc tccattgcat tcatgtacta      4260
ccctcagtct acactcacaa tcatcttctc ccaagactgc tccctttgt tttgtgtttt       4320 tttgagggga attaaggaaa aataagtggg ggcaggtttg gagagctgct tccagtggat      4380
agttgatgag aatcctgacc aaaggaaggc acccttgact gttgggatag acagatggac      4440
ctatggggtg ggaggtggtg tcccttcac actgtgtgt ctcttgggga aggatctccc       4500
cgaatctcaa taaaccagtg aacagtgtga ctcggcaaaa aaaaaaa                    4547

<210> SEQ ID NO 5
<211> LENGTH: 4297
<212> TYPE: DNA
<213> ORGANISM: Homo sapiens

<400> SEQUENCE: 5
cgttcctttc ctcctcgagg ttgcatcccc cctcccctcc ccgcccctcc gactgtcgct        60
cccacctcgg cgctcgcttc cctccccgcc cccttcctgc ctccccagct cccgcccgcc       120
cccccacccc ccgctgccgc gcgccgcccg tgacgtcaga gccccctccc agccccacat       180
ctccctcctg ctcctcctcc tccccctccgt cggtcagtca gtccgcgagg agagtccgcg      240
gtggcggcga cggtggcgag agccgcgggg gccgtaggaa gccaaccttc cctgcttctc      300 cgggccccctc gcccctcct ccccacaaaa tcagggatgg aggcgcctcc ccggcaccct       360
cttagcagcc ctcccagga aaagtgtccc cctgagctc ctaacgctcc caacagcta         420 ccctgccc cacgccatg ggccggggg ccttttgc ccgggtgggg tggccactgc             480
cgcttctggt tgtgatggcg gcaggggtgg ctccggtgtg ggcctccac tccccccatc        540 tcccgcggcc tcactcgcgg gtcccccgc acccctcctc agaacggcgc gcagtgtaca        600
```

-continued

| | |
|---|---|
| tcggggcact gtttcccatg agcggggct ggccagggg ccaggcctgc cagcccgcgg | 660 |
| tggagatggc gctggaggac gtgaatagcc gcagggacat cctgccggac tatgagctca | 720 |
| agctcatcca ccacgacagc aagtgtgatc caggccaagc caccaagtac ctatatgagc | 780 |
| tgctctacaa cgaccctatc aagatcatcc ttatgcctgg ctgcagctct gtctccacgc | 840 |
| tggtggctga ggctgctagg atgtggaacc tcattgtgct ttcctatggc tccagctcac | 900 |
| cagccctgtc aaaccggcag cgtttcccca ctttcttccg aacgcaccca tcagccacac | 960 |
| tccacaaccc tacccgcgtg aaactctttg aaaagtgggg ctggaagaag attgctacca | 1020 |
| tccagcagac cactgaggtc ttcacttcga ctctggacga cctggaggaa cgagtgaagg | 1080 |
| aggctggaat tgagattact ttccgccaga gtttcttctc agatccagct gtgcccgtca | 1140 |
| aaaacctgaa cgccaggat gcccgaatca tcgtgggact tttctatgag actgaagccc | 1200 |
| ggaaagtttt ttgtgaggtg tacaaggagc gtctctttgg gaagaagtac gtctggttcc | 1260 |
| tcattgggtg gtatgctgac aattggttca agatctacga cccttctatc aactgcacag | 1320 |
| tggatgagat gactgaggcg gtggagggcc acatcacaac tgagattgtc atgctgaatc | 1380 |
| ctgccaatac ccgcagcatt tccaacatga catcccagga atttgtggag aaactaacca | 1440 |
| agcgactgaa aagacaccct gaggagacag gaggcttcca ggaggcaccg ctggcctatg | 1500 |
| atgccatctg ggccttggca ctggccctga caagacatc tggaggaggc ggccgttctg | 1560 |
| gtgtgcgcct ggaggacttc aactacaaca accagaccat taccgaccaa atctaccggg | 1620 |
| caatgaactc ttcgtccttt gagggtgtct ctggccatgt ggtgtttgat gccagcggct | 1680 |
| ctcggatggc atggacgctt atcgagcagc ttcagggtgg cagctacaag aagattggct | 1740 |
| actatgacag caccaaggat gatctttcct ggtccaaaac agataaatgg attggagggt | 1800 |
| ccccccccagc tgaccagacc ctggtcatca agacattccg cttcctgtca cagaaactct | 1860 |
| ttatctccgt ctcagttctc tccagcctgg gcattgtcct agctgttgtc tgtctgtcct | 1920 |
| ttaacatcta caactcacat gtccgttata tccagaactc acagcccaac ctgaacaacc | 1980 |
| tgactgctgt gggctgctca ctggctttag ctgctgtctt ccccctgggg ctcgatggtt | 2040 |
| accacattgg gaggaaccag tttcctttcg tctgccaggc ccgcctctgg ctcctgggcc | 2100 |
| tgggctttag tctgggctac ggttccatgt tcaccaagat ttggtgggtc cacacggtct | 2160 |
| tcacaaagaa ggaagaaaag aaggagtgga ggaagactct ggaaccctgg aagctgtatg | 2220 |
| ccacagtggg cctgctggtg ggcatggatg tcctcactct cgccatctgg cagatcgtgg | 2280 |
| accctctgca ccgaccatt gagacatttg ccaaggagga acctaaggaa gatattgacg | 2340 |
| tctctattct gccccagctg gagcattgca gctccaggaa gatgaataca tggcttggca | 2400 |
| ttttctatgg ttacaagggg ctgctgctgc tgctgggaat cttccttgct tatgagacca | 2460 |
| agagtgtgtc cactgagaag atcaatgatc accgggctgt gggcatggct atctacaatg | 2520 |
| tggcagtcct gtgcctcatc actgctcctg tcaccatgat tctgtccagc cagcaggatg | 2580 |
| cagcctttgc cttttgcctct cttgccatag ttttctcctc ctatatcact cttgttgtgc | 2640 |
| tctttgtgcc caagatgcgc aggctgatca cccgagggga atggcagtcg gaggcgcagg | 2700 |
| acaccatgaa gacagggtca tcgaccaaca caacgaggag ggagaagtcc cggctgttgg | 2760 |
| agaaggagaa ccgtgaactg gaaaagatca ttgctgagaa agaggagcgt gtctctgaac | 2820 |
| tgcgccatca actccagtct cggcagcagc tccgctcccg gcgccaccca ccgacacccc | 2880 |
| cagaaccctc tggggcctg cccagggac cccctgagcc ccccgaccgg cttagctgtg | 2940 |
| atgggagtcg agtgcatttg ctttataagt gagggtaggg tgagggagga caggccagta | 3000 |

| | | | | |
|---|---|---|---|---|
| gggggaggga | aagggagagg | ggaagggcag | gggactcagg | aagcaggggg | tccccatccc | 3060 |
| cagctgggaa | gaacatgcta | tccaatctca | tctcttgtaa | atacatgtcc | ccctgtgagt | 3120 |
| tctgggctga | tttgggtctc | tcatacctct | gggaaacaga | ccttttttctc | tcttactgct | 3180 |
| tcatgtaatt | ttgtatcacc | tcttcacaat | ttagttcgta | cctggcttga | agctgctcac | 3240 |
| tgctcacacg | ctgcctcctc | agcagcctca | ctgcatcttt | ctcttcccat | gcaacaccct | 3300 |
| cttctagtta | ccacggcaac | ccctgcagct | cctctgcctt | tgtgctctgt | tcctgtccag | 3360 |
| caggggtctc | ccaacaagtg | ctcttttccac | cccaaggggg | cctctccttt | tctccactgt | 3420 |
| cataatctct | ttccatctta | cttgcccttc | tatactttct | cacatgtggc | tcccctgaa | 3480 |
| ttttgcttcc | tttgggagct | cattctttc | gccaaggctc | acatgctcct | tgcctctgct | 3540 |
| ctgtgcactc | acgctcagca | cacatgcatc | ctccctctc | ctgcgtgtgc | ccactgaaca | 3600 |
| tgctcatgtg | tacacacgct | tttcccgtat | gctttcttca | tgttcagtca | catgtgctct | 3660 |
| cgggtgccct | gcattcacag | ctacgtgtgc | ccctctcatg | gtcatgggtc | tgcccttgag | 3720 |
| cgtgtttggg | taggcatgtg | caatttgtct | agcatgctga | gtcatgtctt | tcctatttgc | 3780 |
| acacgtccat | gtttatccat | gtactttccc | tgtgtaccct | ccatgtacct | tgtgtacttt | 3840 |
| cttcccttaa | atcatggtat | tcttctgaca | gagccatatg | taccctaccc | tgcacattgt | 3900 |
| tatgcacttt | tccccaattc | atgtttggtg | gggccatcca | cccctctcc | ttgtcacaga | 3960 |
| atctccattt | ctgctcagat | tcccccatc | tccattgcat | tcatgtacta | ccctcagtct | 4020 |
| acactcacaa | tcatcttctc | ccaagactgc | tccctttgt | tttgtgtttt | tttgagggga | 4080 |
| attaaggaaa | aataagtggg | ggcaggtttg | gagagctgct | tccagtggat | agttgatgag | 4140 |
| aatcctgacc | aaaggaaggc | acccttgact | gttgggatag | acagatggac | ctatgggtg | 4200 |
| ggaggtggtg | tccctttcac | actgtggtgt | ctcttgggga | aggatctccc | cgaatctcaa | 4260 |
| taaaccagtg | aacagtgtga | ctcggcaaaa | aaaaaaa | | | 4297 |

<210> SEQ ID NO 6
<211> LENGTH: 4361
<212> TYPE: DNA
<213> ORGANISM: Homo sapiens

<400> SEQUENCE: 6

| | | | | |
|---|---|---|---|---|
| ccctctcttc | ccccgcccct | gccttccctt | gcaccctcct | tcttccctcc | gcccgggagc | 60 |
| tctccctggt | ccccggcgcc | gcctccttcc | ctcccggctc | cccgctcccc | gctcccgtgg | 120 |
| ctgccgccgc | cccggggaag | aagagacagg | ggtggggttt | gggggaagcg | agagaggagg | 180 |
| ggagagaccc | tggccaggct | ggagcctgga | ttcgagggga | ggagggacgg | gaggaggaga | 240 |
| aaggtggagg | agaagggagg | ggggagcggg | gaggagcggc | cgggcctggg | gccttgaggc | 300 |
| ccggggagag | ccggggagcc | gggcccgcgc | gccgagatgt | tgctgctgct | gctactggcg | 360 |
| ccactcttcc | tccgcccccc | gggcgcgggc | ggggcgcaga | cccccaacgc | cacctcagaa | 420 |
| ggttgccaga | tcatacaccc | gccctgggaa | ggggcatca | ggtaccgggg | cctgactcgg | 480 |
| gaccaggtga | aggctatcaa | cttcctgcca | gtggactatg | agattgagta | tgtgtgccgg | 540 |
| ggggagcgcg | aggtggtggg | gcccaaggtc | cgcaagtgcc | tggccaacgg | ctcctggaca | 600 |
| gatatgacaa | cacccagccg | ctgtgtgaat | cgaacgccac | actcagaacg | cgcgcgcagtg | 660 |
| tacatcgggg | cactgttttcc | catgagcggg | ggctggccag | ggggccaggc | ctgccagccc | 720 |
| gcggtgagga | tggcgctgga | ggacgtgaat | agccgcaggg | acatcctgcc | ggactatgag | 780 |
| ctcaagctca | tccaccacga | cagcaagtgt | gatccaggcc | aagccaccaa | gtacctatat | 840 |

```
gagctgctct acaacgaccc tatcaagatc atccttatgc ctggctgcag ctctgtctcc      900
acgctggtgg ctgaggctgc taggatgtgg aacctcattg tgctttccta tggctccagc      960
tcaccagccc tgtcaaaccg gcagcgtttc cccactttct tccgaacgca cccatcagcc     1020
acactccaca accctacccg cgtgaaactc tttgaaaagt ggggctggaa gaagattgct     1080
accatccagc agaccactga ggtcttcact tcgactctgg acgacctgga ggaacgagtg     1140
aaggaggctg gaattgagat tactttccgc cagagtttct tctcagatcc agctgtgccc     1200
gtcaaaaacc tgaagcgcca ggatgcccga atcatcgtgg acttttcta tgagactgaa     1260
gcccggaaag tttttgtga ggtgtacaag gagcgtctct ttgggaagaa gtacgtctgg     1320
ttcctcattg ggtggtatgc tgacaattgg ttcaagatct acgacccttc tatcaactgc     1380
acagtggatg agatgactga ggcggtggag ggccacatca aactgagat tgtcatgctg     1440
aatcctgcca ataccccgcag catttccaac atgacatccc aggaatttgt ggagaaacta     1500
accaagcgac tgaaaagaca ccctgaggag acaggaggct tccaggaggc accgctggcc     1560
tatgatgcca tctgggcctt ggcactggcc ctgaacaaga catctggagg aggcggccgt     1620
tctggtgtgc gcctggagga cttcaactac aacaaccaga ccattaccga ccaaatctac     1680
cgggcaatga actcttcgtc ctttgagggt gtctctggcc atgtggtgtt tgatgccagc     1740
ggctctcgga tggcatggac gcttatcgag cagcttcagg gtggcagcta caagaagatt     1800
ggctactatg acagcaccaa ggatgatctt tcctggtcca aaacagataa atggattgga     1860
gggtccccc cagctgacca gaccctggtc atcaagacat ccgcttcct gtcacagaaa     1920
ctctttatct ccgtctcagt tctctccagc ctgggcattg tcctagctgt tgtctgtctg     1980
tcctttaaca tctacaactc acatgtccgt tatatccaga actcacagcc caacctgaac     2040
aacctgactg ctgtgggctg ctcactggct ttagctgctg tcttcccct ggggctcgat     2100
ggttaccaca ttgggaggaa ccagtttcct ttcgtctgcc aggcccgcct ctggctcctg     2160
ggcctgggct ttagtctggg ctacggttcc atgttcacca agatttggtg ggtccacacg     2220
gtcttcacaa agaaggaaga aaagaaggag tggaggaaga ctctggaacc ctggaagctg     2280
tatgccacag tgggcctgct ggtgggcatg gatgtcctca ctctcgccat ctggcagatc     2340
gtggaccctc tgcaccggac cattgagaca tttgccaagg aggaacctaa ggaagatatt     2400
gacgtctcta ttctgcccca gctggagcat tgcagctcca ggaagatgaa tacatggctt     2460
ggcatttct atggttacaa ggggctgctg ctgctgctgg aatcttcct tgcttatgag     2520
accaagagtg tgtccactga aagatcaat gatcaccggg ctgtgggcat ggctatctac     2580
aatgtggcag tcctgtgcct catcactgct cctgtcacca tgattctgtc cagccagcag     2640
gatgcagcct ttgcctttgc ctctcttgcc atagttttct cctcctatat cactcttgtt     2700
gtgctctttg tgcccaagat gcgcaggctg atcacccgag gggaatggca gtcggaggcg     2760
caggacacca tgaagacagg gtcatcgacc aacaacaacg aggaggagaa gtcccggctg     2820
ttggagaagg agaaccgtga actggaaaag atcattgctg agaaagagga gcgtgtctct     2880
gaactgcgcc atcaactcca gtctcggcag cagctccgct cccggcgcca cccaccgaca     2940
cccccagaac cctctggggg cctgcccagg ggacccctg agcccccga ccggcttagc     3000
tgtgatggga gtcgagtgca tttgctttat aagtgagggt agggtgaggg aggacaggcc     3060
agtaggggga gggaaaggga gagggaagg gcagggact caggaagcag ggggtcccca     3120
tccccagctg ggaagaacat gctatccaat ctcatctctt gtaaatacat gtccccctgt     3180
gagttctggg ctgatttggg tctctcatac ctctgggaaa cagaccttt tctctcttac     3240
```

```
tgcttcatgt aattttgtat cacctcttca caatttagtt cgtacctggc ttgaagctgc    3300
tcactgctca cacgctgcct cctcagcagc ctcactgcat cttctcttc ccatgcaaca    3360 ccctcttcta gttaccacgg caacccctgc agctcctctg cctttgtgct ctgttcctgt    3420
ccagcagggg tctcccaaca agtgctcttt ccacccaaa ggggcctctc cttttctcca    3480
ctgtcataat ctctttccat cttacttgcc cttctatact ttctcacatg tggctccccc    3540
tgaattttgc ttcctttggg agctcattct tttcgccaag gctcacatgc tccttgcctc    3600
tgctctgtgc actcacgctc agcacacatg catcctcccc tctcctgcgt gtgcccactg    3660
aacatgctca tgtgtacaca cgcttttccc gtatgctttc ttcatgttca gtcacatgtg    3720
ctctcgggtg ccctgcattc acagctacgt gtgccctct catggtcatg ggtctgccct    3780
tgagcgtgtt tgggtaggca tgtgcaattt gtctagcatg ctgagtcatg tctttcctat    3840
ttgcacacgt ccatgtttat ccatgtactt tccctgtgta ccctccatgt accttgtgta    3900
ctttcttccc ttaaatcatg gtattcttct gacagagcca tatgtaccct accctgcaca    3960
ttgttatgca cttttcccca attcatgttt ggtggggcca tccacaccct ctccttgtca    4020
cagaatctcc atttctgctc agattccccc catctccatt gcattcatgt actaccctca    4080
gtctacactc acaatcatct tctcccaaga ctgctccctt ttgttttgtg ttttttttgag    4140 gggaattaag gaaaaataag tggggcagg tttggagagc tgcttccagt ggatagttga    4200
tgagaatcct gaccaaagga aggcaccctt gactgttggg atagacagat ggacctatgg    4260
ggtgggaggt ggtgtccctt tcacactgtg gtgtctcttg gggaaggatc tccccgaatc    4320
tcaataaacc agtgaacagt gtgactcggc aaaaaaaaaa a                        4361
```

METHODS FOR DIAGNOSING AND TREATING ENCEPHALITIS OR EPILEPSY

CROSS-REFERENCE TO RELATED APPLICATIONS

This application is a National Phase Application of PCT International Application No. PCT/US 10/50746, International Filing Date Sep. 29, 2010, claiming priority to U.S. Provisional Patent Application 61/246,843, filed Sep. 29, 2009, each of which is incorporated by reference herein in its entirety.

FIELD OF THE INVENTION

The invention relates to methods for diagnosing and treating an autoimmune encephalitis or an epilepsy in a subject using an antibody to an inhibitory γ-amino-butyric acid-B ($GABA_B$) receptor.

BACKGROUND OF THE INVENTION

Synaptic plasticity is a fundamental property of neurons that underlie mechanisms of memory, learning, and cognition. Plasticity depends upon the complex interactions of ion channels and synaptic receptors, including the excitatory glutamate N-methyl-D-aspartate receptor (NMDAR) and α-amino-3-hydroxy-5-methyl-4-isoxazolepropionic acid receptor (AMPAR). Animal models of pharmacological or genetic disruption of these receptors result in severe alterations of memory, learning, behavior, and seizures. Therefore it is expected that immune responses against extracellular domains of these receptors would result in similar symptoms. Indeed, two recently identified disorders associated with antibodies to extracellular epitopes of the NR1 subunit of the NMDAR and the G1uR1/2 subunits of the AMPAR result in encephalitides that manifest with prominent psychiatric, behavioral, and memory problems, often accompanied by seizures. In these two synaptic autoimmunities each antibody causes a dramatic and specific decrease of the levels of the target receptor in cultured neurons, suggesting they are pathogenic. Additionally, the neurological syndromes often respond to treatment, and in some patients the immune response occurs as a paraneoplastic manifestation of a tumor that expresses the target receptor, resembling in many aspects the autoimmune disorders of the neuromuscular synapse (e.g., Lambert-Eaton syndrome and myasthenia gravis). These findings along with a remarkable antibody-syndrome specificity and high frequency of some disorders (e.g., anti-NMDAR encephalitis) have drawn attention to other syndromes in which memory and behavior are impaired and seizures occur frequently. In some of these syndromes an immune mediated pathogenesis is suggested by the clinical response to empiric immunotherapy, the CSF an MRI findings suggesting limbic encephalitis, or the detection of antibodies to yet unknown extracellular neuronal antigens.

A better understanding of the function of various antigens may help improve the treatment strategies. For the clinician who currently confronts these patients, however, the best chance to affect the neurologic outcome depends on: (1) the prompt diagnosis of the disorder, (2) the early discovery and treatment of the tumor, and (3) the use of immunotherapy. Accordingly, a need exists for improved methods of diagnosing and treating autoimmune encephalitis or epileptic seizures.

SUMMARY OF THE INVENTION

In one embodiment, the present invention provides a method for diagnosing an encephalitis in a subject, comprising the steps of: obtaining a biological sample from said subject; and testing said biological sample to determine the presence of an antibody to a $GABA_B$ receptor, whereby the presence of said antibody in said biological sample indicates an autoimmune encephalitis, thereby determining a cause of an encephalitis in said subject. In an exemplary embodiment, said antibody binds to the B1 subunit of a $GABA_B$ receptor.

In another embodiment, the present invention provides a method for diagnosing an occult tumor associated with an autoimmune encephalitis in a subject, comprising the steps of: obtaining a biological sample from said subject; and testing said biological sample to determine the presence of an antibody to a $GABA_B$ receptor, whereby the presence of said antibody in said biological sample indicates the presence of said occult tumor in said subject and that said tumor is a cause of said autoimmune encephalitis.

In another embodiment, the present invention provides a method for diagnosing an epilepsy in a subject, comprising the steps of: obtaining a biological sample from said subject; and testing said biological sample to determine the presence of an antibody to a $GABA_B$ receptor, whereby the presence of said antibody in said biological sample indicates the presence of a tumor in said subject and said tumor is a cause of said epilepsy, thereby diagnosing said epilepsy in said subject.

In another embodiment, the present invention provides a method for diagnosing a tumor in a subject having an epilepsy, comprising the step of: obtaining a biological sample from said subject; and testing said biological sample to determine the presence of an antibody to a $GABA_B$ receptor, whereby the presence of said antibody in said biological sample indicates the presence of a tumor in said subject, thereby diagnosing said tumor in said subject having said epilepsy.

In another embodiment, the present invention provides a method for treating an autoimmune encephalitis in a subject, comprising the steps of: detecting a tumor associated with said autoimmune encephalitis by testing a body fluid from said subject for an antibody to a $GABA_B$ receptor, whereby the presence of said antibody in said body fluid indicates the presence of said tumor in said subject and that said tumor is a cause of said autoimmune encephalitis; and treating said tumor.

In another embodiment, the present invention provides a method for detecting an antibody to a $GABA_B$ receptor, whereby the detection of said antibody leads to treatment of an epilepsy or encephalitis with immunotherapy.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

FIG. 2 shows an immunolabeling of rat brain with patient's antibodies. Sagittal section of rat brain immunostained with CSF antibodies of a patient with limbic encephalitis. The extensive staining was observed in the neuropil of hippocampus, thalamus, cerebellum and cerebral cortex.

FIG. 4 shows that patient's antibodies specifically recognize the $GABA_B$ receptor in neuronal synapses. Confocal image of a cultured embryonic rat hippocampal neuron triple labeled with patient's antibodies (green), a guinea pig polyclonal antibody against an intracellular epitope of $GABA_{B1}$ receptor (red), and the presynaptic marker bassoon (blue) (A). Area of dendrite from the same neuron showing patient's antibody staining (B), guinea pig polyclonal $GABA_{B1}$ receptor antibody staining (C), both patient and guinea pig antibody staining (D), and triple stained (E). Quantification of the co-localization of labeling of the dendrites of 24 neurons is shown in (F).

FIG. 6 shows expression of $GABA_B$ receptor by small-cell lung cancer. Consecutive sections of two SCLCs immunostained with a polyclonal antibody against $GABA_{B1}$ receptor and biotinylated IgG from a patient with $GABA_{B1}$ receptor antibodies. Both antibodies show heterogeneous immunostaining indicating expression of $GABA_{B1}$ receptor in both SCLCs (A-D). Avidin-biotin peroxidase method; sections mildly counterstained with hematoxylin; x400.

DETAILED DESCRIPTION OF THE INVENTION

Figure 1A:
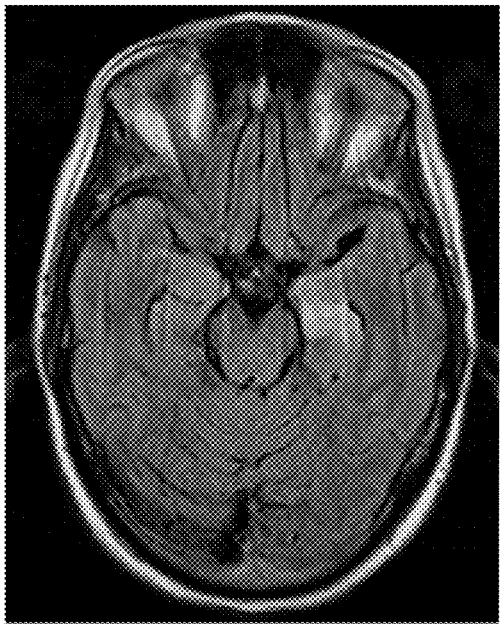
FIG. 1 shows an MRI of a patient with $GABA_B$ receptor antibodies and limbic encephalitis. Axial FLAIR brain MRIs from case 1, taken at presentation (A) showed increased signal in the medial temporal lobes (arrows), more pronounce on the left. Repeat study at 1-month (B) showed improvement. Repeat studies at 3-, and 9-months after presentation (C,D) were stable.

The invention relates to methods for diagnosing and treating an autoimmune encephalitis or an epilepsy in a subject using an antibody to a $GABA_B$ receptor.

In one embodiment, provided herein is a method for diagnosing an encephalitis in a subject, comprising the steps of: obtaining a biological sample from said subject; and testing said biological sample to determine the presence of an antibody to a $GABA_B$ receptor, whereby the presence of said antibody in said biological sample indicates an autoimmune encephalitis, thereby determining a cause of an encephalitis in said subject. In another embodiment, provided herein is a method for diagnosing a tumor associated with an autoimmune encephalitis in a subject, comprising the steps of: obtaining a biological sample from said subject; and testing said biological sample to determine the presence of an antibody to a $GABA_B$ receptor, whereby the presence of said antibody in said biological sample indicates the presence of an occult tumor in said subject and that said tumor is a cause of said autoimmune encephalitis.

In another embodiment, provided herein is a method for diagnosing epilepsy in a subject, comprising the steps of: obtaining a biological sample from said subject; and testing said biological sample to determine the presence of an antibody to a $GABA_B$ receptor, whereby the presence of said antibody in said biological sample indicates the presence of a tumor in said subject and said tumor is a cause of said epilepsy, thereby diagnosing said epilepsy in said subject. In another embodiment, provided herein is a method for diagnosing a tumor in a subject having an epilepsy, comprising the step of: obtaining a biological sample from said subject; and testing said biological sample to determine the presence of an antibody to a $GABA_B$ receptor, whereby the presence of said antibody in said biological sample indicates the presence of a tumor in said subject, thereby diagnosing said tumor in said subject having said epilepsy.

In another embodiment, provided herein is a method for treating an autoimmune encephalitis in a subject, comprising the steps of: detecting a tumor associated with said autoimmune encephalitis by testing a body fluid from said subject for an antibody to a $GABA_B$ receptor, whereby the presence of said antibody in said body fluid indicates the presence of said tumor in said subject and that said tumor is a cause of said autoimmune encephalitis; and treating said tumor.

In one embodiment, the present invention provides a method of determining a cause of an encephalitis in a subject, comprising the step of testing a body fluid of the subject for an antibody to a $GABA_B$ receptor, thereby determining a cause of an encephalitis in a subject. In another embodiment, the presence of an antibody to the B1 subunit of a $GABA_B$ receptor in the body fluid indicates that the encephalitis is of autoimmune etiology. In another embodiment, the presence of an antibody to the B2 subunit of a $GABA_B$ receptor in the body fluid indicates that the encephalitis is of autoimmune etiology. Each possibility represents a separate embodiment of the present invention.

In another embodiment, the methods and compositions provided herein facilitate the recognition of a severe form of autoimmune encephalitis that is often responsive to treatment. In another embodiment, the methods and compositions described herein emphasize the idea that autoimmunity can affect behavior, and particularly that an antibody to a $GABA_B$ receptor may alter emotion, in one embodiment, or memory, consciousness or their compbination in other independent embodiments.

In another embodiment, the present invention provides a method of determining a cause of an autoimmune encephalitis in a subject, comprising the step of testing a body fluid of the subject for an antibody to a $GABA_B$ receptor, thereby determining a cause of an autoimmune encephalitis in a subject. In another embodiment, the presence of the antibody indicates the presence of a tumor in the subject. In another embodiment, the tumor is a cause of the autoimmune encephalitis. Each possibility represents a separate embodiment of the present invention.

In another embodiment, the present invention provides a method of diagnosing an autoimmune encephalitis in a subject, comprising the step of testing a body fluid of the subject for an antibody to the B1 subunit of a $GABA_B$ receptor, thereby diagnosing said autoimmune encephalitis in said subject.

The biological sample used in the methods described herein is a body fluid that is tested by methods of the present invention is, in another embodiment, a cerebro-spinal fluid (CSF). In another embodiment, the body fluid is plasma. In another embodiment, the body fluid is any other type of fluid known in the art. Each possibility represents a separate embodiment of the present invention. In another embodiment, the biological sample is amniotic fluids, blood, sera, saliva, or their combination in another embodiment.

The encephalitis of methods and compositions of the present invention is, in another embodiment, an autoimmune encephalitis. In one embodiment, the autoimmune encephalitis is a paraneoplastic encephalitis. In another embodiment, the autoimmune encephalitis is a non-paraneoplastic encephalitis. In another embodiment, the autoimmune encephalitis is a paraneoplastic autoimmune encephalitis. In another embodiment, the autoimmune encephalitis is a non-paraneoplastic, autoimmune encephalitis. In another embodiment, the autoimmune encephalitis is any other type of autoimmune encephalitis known in the art. Each possibility represents a separate embodiment of the present invention.

In one embodiment, the frequency of paraneoplastic anti-$GABA_B$ encephalitis, diagnosed by the methods described herein, is unknown. In another embodiment paraneoplastic anti-$GABA_B$ encephalitis is frequently unrecognized. This may be due to several features that make this disorder unique among paraneoplastic encephalitis, including in one embodiment, involvement of relatively young women between the $2^{nd}$ and $5^{th}$ decades, or, in another embodiment, the unusual presentation with prominent psychiatric manifestations, or in another embodiment, normal or atypical MRI findings, which in 75% of cases consist of mild, transient T2 or FLAIR abnormalities outside the medial temporal lobes, with cortical enhancement in certain embodiments, or in yet another embodiment, the benign appearance of the ovarian tumors. In one embodiment, any of the subjects presenting the symptoms described hereinabove are diagnosed using the methods described herein.

In another embodiment, the autoimmune encephalitis is a limbic encephalitis. In another embodiment, the autoimmune encephalitis is associated with a limbic dysfunction. In another embodiment, the autoimmune encephalitis is not associated with a limbic dysfunction. Each possibility represents a separate embodiment of the present invention.

In one embodiment, limbic encephalitis causes impressive deficits that are characteristically dominated by rapid and severe loss of short-term memory. In another embodiment, patients show subacute encephalitis of later adult life, mainly affecting the limbic areas with evidence of cancer in one embodiment. In one embodiment, the term "limbic encephalitis" refers to a subject exhibiting severe short-term memory loss and dementia in association with bronchial carcinoma.

In another embodiment, the autoimmune encephalitis of methods and compositions of the present invention is associated with seizures. In another embodiment, the autoimmune encephalitis is associated with a diencephalic syndrome. In another embodiment, the autoimmune encephalitis is associated with a psychiatric symptom. In another embodiment, the autoimmune encephalitis is associated with an abnormality in cognition. In another embodiment, the autoimmune encephalitis is associated with an abnormality in behavior.

In another embodiment, the autoimmune encephalitis is associated with amnesia. In another embodiment, the autoimmune encephalitis is associated with a memory deficit. In another embodiment, the autoimmune encephalitis is associated with memory problems. In another embodiment, the autoimmune encephalitis is associated with a hypokinetic syndrome.

In another embodiment, the autoimmune encephalitis is associated with a movement disorder. In another embodiment, the autoimmune encephalitis is associated with abnormal movements. In another embodiment, the movement disorder is any other movement disorder known in the art. Each possibility represents a separate embodiment of the present invention.

In another embodiment, the autoimmune encephalitis is associated with a decreased level of consciousness. In another embodiment, the autoimmune encephalitis is associated with hypoventilation.

In another embodiment, the autoimmune encephalitis is associated with, dysfunction of any part of the brain or spinal cord. In another embodiment, the autoimmune encephalitis is associated with a combination of any of the above symptoms or disorders. Each type of encephalitis represents a separate embodiment of the present invention.

In one embodiment, the autoimmune encephalitis is associated with a tumor. In one embodiment, the tumor is a neuroendocrine tumor of the lung or small cell lung cancer (SCLC). In another embodiment, the tumor is an ovarian teratoma. In another embodiment, the tumor is a thymic tumor.

In another embodiment, the tumor is a testicular tumor. In another embodiment, the cancer associated with the encephalitis is a cervical cancer tumor. In another embodiment, the cancer is a head and neck cancer tumor. In another embodiment, the cancer is a breast cancer tumor. In another embodiment, the cancer is an ano-genital cancer tumor.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is a mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma.

In another embodiment, the tumor is any other type of tumor known in the art. Each possibility represents a separate embodiment of the present invention.

In another embodiment, the present invention provides a method of determining a cause of an epilepsy in a subject, comprising the step of testing a body fluid of said subject for an antibody to a $GABA_B$ receptor, thereby determining a cause of said epilepsy in said subject. In another embodiment, the antibody indicates a presence of a tumor in the subject. In another embodiment, the tumor is a cause of the epilepsy. Each possibility represents a separate embodiment of the present invention.

The epilepsy of methods and compositions of the present invention is, in another embodiment, an idiopathic epilepsy. In another embodiment, the epilepsy responds to IgG-depleting therapy. In another embodiment, the epilepsy is associated with partial seizures. In another embodiment, the epilepsy is associated with simple partial seizures. In another embodiment, the epilepsy is associated with complex partial seizures. In another embodiment, the epilepsy is associated with generalized seizures. In another embodiment, the epilepsy is associated with absence (petit mal) seizures. In another embodiment, the epilepsy is associated with myoclonic seizures. In another embodiment, the epilepsy is associated with tonic-clonic (grand mal) seizures.

In another embodiment, the epilepsy is associated with West syndrome. In another embodiment, the epilepsy is associated with Lennox-Gastaut syndrome. In another embodiment, the epilepsy is associated with any other syndrome known in the art.

In another embodiment the epilepsy is of no known cause. In another embodiment the epilepsy is any other type of epilepsy known in the art. Each type of epilepsy represents a separate embodiment of the present invention.

"Cause of" an autoimmune encephalitis, epilepsy, etc, refers, in another embodiment, to a primary cause of the disorder. In another embodiment, the term refers to a contributing cause of the disorder. In another embodiment, the term refers to an indirect causation. In another embodiment, the term refers to causation via an immune response induced by the tumor. In another embodiment, the term refers to a significant cause of the disorder. Each possibility represents a separate embodiment of the present invention.

In another embodiment, the present invention provides a method for diagnosing a tumor in a subject having an encephalitis, comprising the step of testing a body fluid of said subject for an antibody to a $GABA_B$ receptor, thereby diagnosing a tumor in said subject having said encephalitis. In another embodiment, the presence of the antibody indicates a presence of a tumor in the subject. Each possibility represents a separate embodiment of the present invention.

In another embodiment, the present invention provides a method for detecting a tumor in a subject having an encephalitis, comprising the step of testing a body fluid of said subject for an antibody to a $GABA_B$ receptor, thereby detecting said tumor in said subject having said encephalitis. In another embodiment, the presence of the antibody indicates the presence of a tumor in the subject. Each possibility represents a separate embodiment of the present invention.

In one embodiment, the present invention provides a method for diagnosing a tumor in a subject having an epilepsy, comprising the step of testing a body fluid of said subject for an antibody to a $GABA_B$ receptor, thereby diagnosing said tumor in said subject having said epilepsy. In another embodiment, the presence of the antibody indicates the presence of a tumor in the subject. Each possibility represents a separate embodiment of the present invention.

In one embodiment, the present invention provides a method for detecting a tumor in a subject having an epilepsy, comprising the step of testing a body fluid of said subject for an antibody to a $GABA_B$ receptor, thereby detecting said tumor in said subject having said epilepsy. In another embodiment, the presence of said antibody indicates a presence of a tumor in the subject. Each possibility represents a separate embodiment of the present invention.

In one embodiment, the present invention provides a method of diagnosing or detecting a $GABA_B$-mediated disease in a subject, comprising the step of testing a body fluid of the subject for an antibody to an antibody to a $GABA_B$ receptor, thereby diagnosing or detecting said $GABA_B$-mediated disease in said subject.

$GABA_B$ receptors mediate presynaptic inhibition by two mechanisms: the activation of G-protein-coupled-inward-rectifying potassium (GIRK) channels and the inhibition of calcium channels. They also attenuate presynaptic firing frequencies. At the post-synapse, the $GABA_B$ receptors mediate inhibition by similar mechanisms and by inducing a slow inhibitory post-synaptic potential (IPSP). On a neuronal network level, $GABA_B$ receptors modulate their activity by limiting the duration of network high-activity states, preventing excessive neuronal synchronization, and allowing novel stimuli to break synchronous activity. $GABA_B$ receptors are widely distributed in the brain and spinal cord, but are particularly abundant in the hippocampus, thalamus and cerebellum, which are the areas of more intense rat brain immunolabeling by patients' antibodies. The main autoantigen of patients' antibodies, the $GABA_{B1}$ subunit is necessary for GABA binding (and receptor function) while the $GABA_{B2}$ subunit is required for localization of the receptor to appropriate areas of the cell membrane and for G-protein coupling. Deletion of $GABA_{B1}$ in transgenic mice results in predominant seizures, memory deficits, and increased anxiety behaviors. Both genetic and pharmacologic evidence supports an important role for GABA$_B$ receptors in controlling anxiety and regulating mood.

In one embodiment, the invention provides a method of treating autoimmune encephalitis in a subject. In one embodiment, the method comprises the steps of: detecting a tumor associated with an autoimmune encephalitis by testing a body fluid from said subject for an antibody to a GABA$_B$ receptor, whereby a presence of said antibody indicates the presence of said tumor in said subject and that said tumor is a cause of said autoimmune encephalitis. In another embodiment, the method comprises the step of treating said tumor. In another embodiment, the tumor is treated during the early stage. In another embodiment, the tumor is treated within four months of the onset of a symptom associated with autoimmune encephalitis. In another embodiment, the tumor is treated within three months of the onset of a symptom associated with autoimmune encephalitis. In another embodiment, the tumor is treated within two months of the onset of a symptom associated with autoimmune encephalitis. In another embodiment, the tumor is treated within one month of the onset of a symptom associated with autoimmune encephalitis.

In one embodiment, the step of treating said tumor comprises removing said tumor. In another embodiment, the step of treating said tumor comprises immunotherapy. In another embodiment, the step of treating said tumor comprises removing said tumor in combination with immunotherapy. In another embodiment, the step of treating said tumor comprises chemotherapy. In another embodiment, the step of treating said tumor comprises removing said tumor in combination with chemotherapy.

In one embodiment, GABA$_B$ receptor comprises subunits. In another embodiment, GABA$_B$ receptors are formed from heteromers of B1 and B2 subunits. In another embodiment, both subunits are required to create a functional receptor that contains B1 and B2 subunits.

The B1 subunit of methods and compositions of the present invention is, in another embodiment, a B 1-a subunit. In another embodiment, the receptor exists as heteromers of B1 subunits and B2 subunits. In one embodiment, B1 and B2 combine to form receptor subtypes with distinct pharmacological properties, localization, and ability to interact with intracellular messengers.

In another embodiment, the B1 subunit is a monomer of a multimer of GABA$_B$ receptor. In another embodiment, the multimer is a homomer that comprises two or more subunits. In another embodiment, the multimer is a homo-dimer that comprises two B1 subunits. In another embodiment, the multimer is a heteromer that comprises a B1 subunit. In another embodiment, the multimer is a heteromer that comprises a B1 subunit and a B2 subunit. In another embodiment, the multimer is a heteromer that comprises a B1-a subunit and B2 subunit. In another embodiment, the multimer is a heteromer that comprises B1-b subunit and a B2 subunit. In another embodiment, the multimer is a heteromer that comprises B 1-c subunit and a B2 subunit.

In one embodiment, the B1 subunit of GABA$_B$ receptor has the sequence as set forth below:

```
                                                              (SEQ ID NO: 1)
           MLLLLLLAPL  FLRPPGAGGA  QTPNATSEGC  QIIHPPWEGG  IRYRGLTRDQ  VKAINFLPVD     60

YEIEYVCRGE  REVVGPKVRK  CLANGSWTDM  DTPSRCVRIC  SKSYLTLENG  KVFLTGGDLP    120

ALDGARVDFR  CDPDFHLVGS  SRSICSQGQW  STPKPHCQVN  RTPHSERRAV  YIGALFPMSG    180

GWPGGQACQP  AVEMALEDVN  SRRDILPDYE  LKLIHHDSKC  DPGQATKYLY  ELLYNDPIKI    240

ILMPGCSSVS  TLVAEAARMW  NLIVLSYGSS  SPALSNRQRF  PTFFRTHPSA  TLHNPTRVKL    300

FEKWGWKKIA  TIQQTTEVFT  STLDDLEERV  KEAGIEITFR  QSFFSDPAVP  VKNLKRQDAR    360

IIVGLFYETE  ARKVFCEVYK  ERLFGKKYVW  FLIGWYADNW  FKIYDPSINC  TVDEMTEAVE    420

GHITTEIVML  NPANTRSISN  MTSQEFVEKL  TKRLKRHPEE  TGGFQEAPLA  YDAIWALALA    480

LNKTSGGGGR  SGVRLEDFNY  NNQTITDQIY  RAMNSSSFEG  VSGHVVFDAS  GSRMAWTLIE    540

QLQGGSYKKI  GYYDSTKDDL  SWSKTDKWIG  GSPPADQTLV  IKTFRFLSQK  LFISVSVLSS    600

LGIVLAVVCL  SFNIYNSHVR  YIQNSQPNLN  NLTAVGCSLA  LAAVFPLGLD  GYHIGRNQFP    660

FVCQARLWLL  GLGFSLGYGS  MFTKIWWVHT  VFTKKEEKKE  WRKTLEPWKL  YATVGLLVGM    720

DVLTLAIWQI  VDPLHRTIET  FAKEEPKEDI  DVSILPQLEH  CSSRKMNTWL  GIFYGYKGLL    780

LLLGIFLAYE  TKSVSTEKIN  DHRAVGMAIY  NVAVLCLITA  PVTMILSSQQ  DAAFAFASLA    840

IVFSSYITLV  VLFVPKMRRL  ITRGEWQSEA  QDTMKTGSST  NNNEEEKSRL  LEKENRELEK    900

IIAEKEERVS  ELRHQLQSRQ  QLRSRRHPPT  PPEPSGGLPR  GPPEPPDRLS  CDGSRVHLLY    960

K                                                                       961
```

In another embodiment, the B1 subunit of GABA$_B$ receptor has the sequence as set forth below:

```
                                                        (SEQ ID NO: 2)
MGPGAPFARV GWPLPLLVVM AAGVAPVWAS HSPHLPRPHS RVPPHPSSER RAVYIGALFP    60

MSGGWPGGQA CQPAVEMALE DVNSRRDILP DYELKLIHHD SKCDPGQATK YLYELLYNDP   120

IKIILMPGCS SVSTLVAEAA RMWNLIVLSY GSSSPALSNR QRFPTFFRTH PSATLHNPTR   180

VKLFEKWGWK KIATIQQTTE VFTSTLDDLE ERVKEAGIEI TFRQSFFSDP AVPVKNLKRQ   240

DARIIVGLFY ETEARKVFCE VYKERLFGKK YVWFLIGWYA DNWFKIYDPS INCTVDEMTE   300

AVEGHITTEI VMLNPANTRS ISNMTSQEFV EKLTKRLKRH PEETGGFQEA PLAYDAIWAL   360

ALALNKTSGG GGRSGVRLED FNYNNQTITD QIYRAMNSSS FEGVSGHVVF DASGSRMAWT   420

LIEQLQGGSY KKIGYYDSTK DDLSWSKTDK WIGGSPPADQ TLVIKTFRFL SQKLFISVSV   480

LSSLGIVLAV VCLSFNIYNS HVRYIQNSQP NLNNLTAVGC SLALAAVFPL GLDGYHIGRN   540

QFPFVCQARL WLLGLGFSLG YGSMFTKIWW VHTVFTKKEE KKEWRKTLEP WKLYATVGLL   600

VGMDVLTLAI WQIVDPLHRT IETFAKEEPK EDIDVSILPQ LEHCSSRKMN TWLGIFYGYK   660

GLLLLLGIFL AYETKSVSTE KINDHRAVGM AIYNVAVLCL ITAPVTMILS SQQDAAFAFA   720

SLAIVFSSYI TLVVLFVPKM RRLITRGEWQ SEAQDTMKTG SSTNNNEEEK SRLLEKENRE   780

LEKIIAEKEE RVSELRHQLQ SRQQLRSRRH PPTPPEPSGG LPRGPPEPPD RLSCDGSRVH   840

LLYK                                                               844
```

In another embodiment, the B1 subunit of GABA$_B$ receptor has the sequence as set forth below:

```
                                                        (SEQ ID NO: 3)
MLLLLLLAPL FLRPPGAGGA QTPNATSEGC QIIHPPWEGG IRYRGLTRDQ VKAINFLPVD    60

YEIEYVCRGE REVVGPKVRK CLANGSWTDM DTPSRCVNRT PHSERRAVYI GALFPMSGGW   120

PGGQACQPAV EMALEDVNSR RDILPDYELK LIHHDSKCDP GQATKYLYEL LYNDPIKIIL   180

MPGCSSVSTL VAEAARMWNL IVLSYGSSSP ALSNRQRFPT FFRTHPSATL HNPTRVKLFE   240

KWGWKKIATI QQTTEVFTST LDDLEERVKE AGIEITFRQS FFSDPAVPVK NLKRQDARII   300

VGLFYETEAR KVFCEVYKER LFGKKYVWFL IGWYADNWFK IYDPSINCTV DEMTEAVEGH   360

ITTEIVMLNP ANTRSISNMT SQEFVEKLTK RLKRHPEETG GFQEAPLAYD AIWALALALN   420

KTSGGGGRSG VRLEDFNYNN QTITDQIYRA MNSSSFEGVS GHVVFDASGS RMAWTLIEQL   480

QGGSYKKIGY YDSTKDDLSW SKTDKWIGGS PPADQTLVIK TFRFLSQKLF ISVSVLSSLG   540

IVLAVVCLSF NIYNSHVRYI QNSQPNLNNL TAVGCSLALA AVFPLGLDGY HIGRNQFPFV   600

CQARLWLLGL GFSLGYGSMF TKIWWVHTVF TKKEEKKEWR KTLEPWKLYA TVGLLVGMDV   660

LTLAIWQIVD PLHRTIETFA KEEPKEDIDV SILPQLEHCS SRKMNTWLGI FYGYKGLLLL   720

LGIFLAYETK SVSTEKINDH RAVGMAIYNV AVLCLITAPV TMILSSQQDA AFAFASLAIV   780

FSSYITLVVL FVPKMRRLIT RGEWQSEAQD TMKTGSSTNN NEEEKSRLLE KENRELEKII   840

AEKEERVSEL RHQLQSRQQL RSRRHPPTPP EPSGGLPRGP PEPPDRLSCD GSRVHLLYK   899
```

In another embodiment, the B1 subunit is a homologue of SEQ ID NOs: 1, 2, or 3. In another embodiment, the B1 subunit is a variant of SEQ ID NOs: 1, 2, or 3. In another embodiment, the B1 subunit is an isomer of SEQ ID NOs: 1, 2, or 3. In another embodiment, the B1 subunit is a fragment of SEQ ID NOs: 1, 2, or 3. In another embodiment, the B1 subunit comprises SEQ ID NOs: 1, 2, or 3. Each possibility represents a separate embodiment of the present invention.

In another embodiment, the B1 subunit of GABA$_B$ receptor is encoded by a nucleotide sequence having the sequence:

(SEQ ID NO: 4)

```
ccctctcttc ccccgccct gccttcctt gcaccctcct tcttccctcc gcccgggagc      60
tctccctggt ccccggcgcc gcctccttcc ctcccggctc cccgctcccc gctcccgtgg    120
ctgccgccgc cccggggaag aagagacagg ggtgggggttt gggggaagcg agagaggagg   180
ggagagaccc tggccaggct ggagcctgga ttcgagggga ggagggacgg gaggaggaga    240
aaggtggagg agaagggagg ggggagcggg gaggagcggc cgggcctggg gccttgaggc    300
ccggggagag ccggggagcc gggcccgcgc gccgagatgt tgctgctgct gctactggcg    360
ccactcttcc tccgccccc gggcgcgggc ggggcgcaga ccccaacgc cacctcagaa     420
ggttgccaga tcatacaccc gccctgggaa ggggggcatca ggtaccgggg cctgactcgg   480
gaccaggtga aggctatcaa cttcctgcca gtggactatg agattgagta tgtgtgccgg   540
ggggagcgcg aggtggtggg gcccaaggtc cgcaagtgcc tggccaacgg ctcctggaca   600
gatatggaca cacccagccg ctgtgtccga atctgctcca agtcttattt gaccctggaa   660
aatgggaagg ttttcctgac gggtggggac ctcccagctc tggacggagc ccgggtggat  720
ttccggtgtg accccgactt ccatctggtg ggcagctccc ggagcatctg tagtcagggc  780
cagtggagca cccccaagcc ccactgccag gtgaatcgaa cgccacactc agaacggcgc  840
gcagtgtaca tcggggcact gtttcccatg agcgggggct ggccagggggg ccaggcctgc  900
cagcccgcgg tggagatggc gctggaggac gtgaatagcc gcagggacat cctgccggac  960
tatgagctca agctcatcca ccacgacagc aagtgtgatc caggccaagc caccaagtac 1020
ctatatgagc tgctctacaa cgaccctatc aagatcatcc ttatgcctgg ctgcagctct 1080
gtctccacgc tggtggctga ggctgctagg atgtggaacc tcattgtgct ttcctatggc 1140
tccagctcac cagccctgtc aaaccggcag cgtttcccca ctttcttccg aacgcaccca 1200
tcagccacac tccacaaccc tacccgcgtg aaactctttg aaaagtgggg ctggaagaag 1260
attgctacca tccagcagac cactgaggtc ttcacttcga ctctggacga cctggaggaa 1320
cgagtgaagg aggctggaat tgagattact ttccgccaga gtttcttctc agatccagct 1380
gtgcccgtca aaaacctgaa gcgccaggat gcccgaatca tcgtgggact tttctatgag 1440
actgaagccc ggaaagtttt ttgtgaggtg tacaaggagc gtctctttgg aagaagtac  1500
gtctggttcc tcattgggtg gtatgctgac aattggttca agatctacga cccttctatc 1560
aactgcacag tggatgagat gactgaggcg gtggagggcc acatcacaac tgagattgtc 1620
atgctgaatc ctgccaatac ccgcagcatt tccaacatga catcccagga atttgtggag 1680
aaactaacca agcgactgaa aagacaccct gaggagacag gaggcttcca ggaggcaccg 1740
ctggcctatg atgccatctg ggccttggca ctggccctga caagacatc tggaggaggc 1800
ggccgttctg gtgtgcgcct ggaggacttc aactacaaca accagaccat taccgaccaa 1860
atctaccggg caatgaactc ttcgtcccttt gagggtgtct ctggccatgt ggtgtttgat 1920
gccagcgggc tcggatggc atggacgctt atcgagcagc ttcagggtgg cagctacaag 1980
aagattggct actatgacag caccaaggat gatctttcct ggtccaaaac agataaatgg 2040
attggagggt ccccccagc tgaccagacc ctggtcatca agacattccg cttcctgtca 2100
cagaaactct ttatctccgt ctcagttctc tccagcctgg gcattgtcct agctgttgtc 2160
tgtctgtcct ttaacatcta caactcacat gtccgttata tccagaactc acagcccaac 2220
ctgaacaacc tgactgctgt gggctgctca ctggcttag ctgctgtctt cccctgggg  2280
ctcgatggtt accacattgg gaggaaccag tttccttcg tctgccaggc ccgcctctgg 2340
```

-continued

```
ctcctgggcc tgggctttag tctgggctac ggttccatgt tcaccaagat tggtgggtc      2400 cacacggtct tcacaaagaa ggaagaaaag aaggagtgga ggaagactct ggaaccctgg      2460
aagctgtatg ccacagtggg cctgctggtg ggcatggatg tcctcactct cgccatctgg      2520
cagatcgtgg accctctgca ccggaccatt gagacatttg ccaaggagga acctaaggaa      2580
gatattgacg tctctattct gccccagctg gagcattgca gctccaggaa gatgaataca      2640
tggcttggca ttttctatgg ttacaagggg ctgctgctgc tgctgggaat cttccttgct      2700
tatgagacca agagtgtgtc cactgagaag atcaatgatc accgggctgt gggcatggct      2760
atctacaatg tggcagtcct gtgcctcatc actgctcctg tcaccatgat tctgtccagc      2820
cagcaggatg cagcctttgc ctttgcctct cttgccatag ttttctcctc ctatatcact      2880
cttgttgtgc tctttgtgcc caagatgcgc aggctgatca cccgagggga atggcagtcg      2940
gaggcgcagg acaccatgaa gacagggtca tcgaccaaca caacgagga ggagaagtcc       3000 cggctgttgg agaaggagaa ccgtgaactg gaaaagatca ttgctgagaa agaggagcgt      3060
gtctctgaac tgcgccatca actccagtct cggcagcagc tccgctcccg cgccaccca       3120 ccgacacccc cagaaccctc tgggggcctg cccagggggac cccctgagcc ccccgaccgg      3180
cttagctgtg atgggagtcg agtgcatttg ctttataagt gagggtaggg tgagggagga      3240
caggccagta gggggaggga aagggagagg ggaagggcag gggactcagg aagcaggggg      3300
tccccatccc cagctgggaa gaacatgcta tccaatctca tctcttgtaa atacatgtcc      3360
ccctgtgagt tctgggctga tttggtctc tcatacctct gggaaacaga ccttttttctc      3420 tcttactgct tcatgtaatt ttgtatcacc tcttcacaat ttagttcgta cctggcttga      3480
agctgctcac tgctcacacg ctgcctcctc agcagcctca ctgcatcttt ctcttcccat      3540
gcaacaccct cttctagtta ccacggcaac ccctgcagct cctctgcctt tgtgctctgt      3600
tcctgtccag caggggtctc ccaacaagtg ctctttccac cccaaagggg cctctccttt      3660
tctccactgt cataatctct ttccatctta cttgcccttc tatactttct cacatgtggc      3720 tcccctgaa ttttgcttcc tttgggagct cattcttttc gccaaggctc acatgctcct      3780
tgcctctgct ctgtgcactc acgctcagca cacatgcatc ctcccctctc ctgcgtgtgc      3840
ccactgaaca tgctcatgtg tacacacgct tttcccgtat gctttcttca tgttcagtca      3900
catgtgctct cgggtgccct gcattcacag ctacgtgtgc cctctcatg gtcatgggtc      3960 tgcccttgag cgtgtttggg taggcatgtg caatttgtct agcatgctga gtcatgtctt      4020
tcctatttgc acacgtccat gtttatccat gtactttccc tgtgtaccct ccatgtacct      4080
tgtgtacttt cttccttaa atcatggtat tcttctgaca gagccatatg taccctaccc      4140
tgcacattgt tatgcacttt tcccccaattc atgtttggtg gggccatcca caccctctcc      4200
ttgtcacaga atctccattt ctgctcagat tccccccatc tccattgcat tcatgtacta      4260
ccctcagtct acactcacaa tcatcttctc ccaagactgc tccttttgt tttgtgtttt      4320 tttgaggga attaaggaaa aataagtggg ggcaggtttg gagagctgct tccagtggat      4380
agttgatgag aatcctgacc aaaggaaggc acccttgact gttgggatag acagatggac      4440
ctatggggtg ggaggtggtg tccctttcac actgtggtgt ctcttgggga aggatctccc      4500
cgaatctcaa taaaccagtg aacagtgtga ctcggcaaaa aaaaaa                   4547
```

In another embodiment, the B1 subunit of GABA$_B$ receptor is encoded by a nucleotide sequence having the sequence:

(SEQ ID NO: 5)

```
cgttcctttc ctcctcgagg ttgcatcccc cctccctcc ccgccctcc gactgtcgct      60
cccacctcgg cgctcgcttc cctccccgcc cccttcctgc ctcccagct cccgcccgcc    120
cccccacccc ccgctgccgc gcgccgcccg tgacgtcaga gcccctccc agcccacat     180
ctccctcctg ctcctcctcc tccctccgt cggtcagtca gtccgcgagg agagtccgcg    240
gtggcggcga cggtggcgag agccgcgggg gccgtaggaa gccaaccttc cctgcttctc    300
cggggccctc gccccctcct ccccacaaaa tcagggatgg aggcgcctcc ccggcaccct    360
cttagcagcc ctccccagga aaagtgtccc ccctgagctc ctaacgctcc caacagcta    420
cccctgcccc ccacgccatg gggcccgggg ccccttttgc ccgggtgggg tggccactgc    480
cgcttctggt tgtgatggcg gcaggggtgg ctccggtgtg ggcctccac tcccccatc     540
tcccgcggcc tcactcgcgg gtcccccgc acccctcctc agaacggcgc gcagtgtaca    600
tcggggcact gtttcccatg agcggggct ggccaggggg ccaggcctgc cagcccgcgg    660
tggagatggc gctggaggac gtgaatagcc gcagggacat cctgccggac tatgagctca    720
agctcatcca ccacgacagc aagtgtgatc caggccaagc caccaagtac ctatatgagc    780
tgctctacaa cgaccctatc aagatcatcc ttatgcctgg ctgcagctct gtctccacgc    840
tggtggctga ggctgctagg atgtggaacc tcattgtgct ttcctatggc tccagctcac    900
cagccctgtc aaaccggcag cgtttcccca cttcttccg aacgcaccca tcagccacac    960
tccacaaccc tacccgcgtg aaactctttg aaaagtgggg ctggaagaag attgctacca   1020
tccagcagac cactgaggtc ttcacttcga ctctggacga cctggaggaa cgagtgaagg   1080
aggctggaat tgagattact ttccgccaga gtttcttctc agatccagct gtgcccgtca   1140
aaaacctgaa gcgccaggat gcccgaatca tcgtgggact tttctatgag actgaagccc   1200
ggaaagtttt ttgtgaggtg tacaaggagc gtctcttttgg gaagaagtac gtctggttcc   1260
tcattgggtg gtatgctgac aattggttca agatctacga cccttctatc aactgcacag   1320
tggatgagat gactgaggcg gtggagggcc acatcacaac tgagattgtc atgctgaatc   1380
ctgccaatac ccgcagcatt tccaacatga catcccagga atttgtggag aaactaacca   1440
agcgactgaa aagacaccct gaggagacag gaggcttcca ggaggcaccg ctggcctatg   1500
atgccatctg ggccttggca ctggcccctga acaagacatc tggaggaggc ggccgttctg   1560
gtgtgcgcct ggaggacttc aactacaaca accagaccat taccgaccaa atctaccggg   1620
caatgaactc ttcgtccttt gagggtgtct ctggccatgt ggtgtttgat gccagcggct   1680
ctcggatggc atggacgctt atcgagcagc ttcagggtgg cagctacaag aagattggct   1740
actatgacag caccaaggat gatctttcct ggtccaaaac agataaatgg attggagggt   1800
cccccccagc tgaccagacc ctggtcatca agacattccg cttcctgtca cagaaactct   1860
ttatctccgt ctcagttctc tccagcctgg gcattgtcct agctgttgtc tgtctgtcct   1920
ttaacatcta caactcacat gtccgttata tccagaactc acagcccaac ctgaacaacc   1980
tgactgctgt gggctgctca ctggcttag ctgctgtctt ccccctgggg ctcgatggtt    2040
accacattgg gaggaaccag tttcctttcg tctgccaggc ccgcctctgg ctcctgggcc   2100
tgggctttag tctgggctac ggttccatgt tcaccaagat ttggtgggtc cacacggtct   2160
tcacaaagaa ggaagaaaag aaggagtgga ggaagactct ggaaccctgg aagctgtatg   2220
ccacagtggg cctgctggtg ggcatggatg tcctcactct cgccatctgg cagatcgtgg   2280
accctctgca ccggaccatt gagacatttg ccaaggagga acctaaggaa gatattgacg   2340
```

-continued

```
tctctattct gccccagctg gagcattgca gctccaggaa gatgaataca tggcttggca      2400
ttttctatgg ttacaagggg ctgctgctgc tgctgggaat cttccttgct tatgagacca      2460
agagtgtgtc cactgagaag atcaatgatc accgggctgt gggcatggct atctacaatg      2520
tggcagtcct gtgcctcatc actgctcctg tcaccatgat tctgtccagc cagcaggatg      2580
cagcctttgc cttttgcctct cttgccatag ttttctcctc ctatatcact cttgttgtgc     2640
tctttgtgcc caagatgcgc aggctgatca cccgagggga atggcagtcg gaggcgcagg      2700
acaccatgaa gacagggtca tcgaccaaca acaacgagga ggagaagtcc cggctgttgg      2760
agaaggagaa ccgtgaactg gaaaagatca ttgctgagaa agaggagcgt gtctctgaac      2820
tgcgccatca actccagtct cggcagcagc tccgctcccg gcgccaccca ccgacacccc      2880
cagaaccctc tggggggcctg cccaggggac cccctgagcc ccccgaccgg cttagctgtg    2940
atgggagtcg agtgcatttg ctttataagt gagggtaggg tgagggagga caggccagta      3000
gggggaggga aagggagagg ggaagggcag gggactcagg aagcaggggg tccccatccc      3060
cagctgggaa gaacatgcta tccaatctca tctcttgtaa atacatgtcc cctgtgagt       3120 tctgggctga tttgggtctc tcatacctct gggaaacaga cctttttctc tcttactgct      3180
tcatgtaatt ttgtatcacc tcttcacaat ttagttcgta cctggcttga agctgctcac      3240
tgctcacacg ctgcctcctc agcagcctca ctgcatcttt ctcttcccat gcaacaccct      3300
cttctagtta ccacggcaac ccctgcagct cctctgcctt tgtgctctgt tcctgtccag      3360
caggggtctc ccaacaagtg ctcttttccac cccaaagggg cctctccttt tctccactgt    3420
cataatctct ttccatctta cttgcccttc tatactttct cacatgtggc tccccctgaa     3480
ttttgcttcc tttgggagct cattctttcc gccaaggctc acatgctcct tgcctctgct     3540
ctgtgcactc acgctcagca cacatgcatc ctcccctctc ctgcgtgtgc ccactgaaca    3600
tgctcatgtg tacacacgct tttcccgtat gctttcttca tgttcagtca catgtgctct     3660
cgggtgccct gcattcacag ctacgtgtgc ccctctcatg gtcatgggtc tgcccttgag     3720 cgtgttttggg taggcatgtg caatttgtct agcatgctga gtcatgtctt tcctatttgc     3780
acacgtccat gtttatccat gtactttccc tgtgtaccct ccatgtacct tgtgtacttt     3840
cttcccttaa atcatggtat tcttctgaca gagccatatg taccctaccc tgcacattgt    3900
tatgcacttt tcccaattc atgtttggtg gggccatcca caccctctcc ttgtcacaga      3960
atctccattt ctgctcagat tccccccatc tccattgcat tcatgtacta ccctcagtct    4020
acactcacaa tcatcttctc ccaagactgc tcccttttgt tttgtgtttt tttgagggga    4080
attaaggaaa aataagtggg ggcaggtttg gagagctgct tccagtggat agttgatgag    4140
aatcctgacc aaaggaaggc acccttgact gttgggatag acagatggac ctatgggtg     4200 ggaggtggtg tccctttcac actgtggtgt ctcttggga aggatctccc cgaatctcaa     4260
taaaccagtg aacagtgtga ctcggcaaaa aaaaaaa                              4297
```

In another embodiment, the B1 subunit of GABA$_B$ receptor is encoded by a nucleotide sequence having the sequence:

```
                                                       (SEQ ID NO: 6)
ccctctcttc ccccgcccct gccttcccctt gcaccctcct tcttccctcc gccgggagc       60 tctccctggt cccggcgcc gcctccttcc ctcccggctc ccgctccccc gctcccgtgg      120
ctgccgccgc cccgggaag aagagacagg ggtgggggttt gggggaagcg agagaggagg     180
ggagagaccc tggccaggct ggagcctgga ttcgaggga ggagggacgg gaggaggaga      240
```

-continued

```
aaggtggagg agaagggagg ggggagcggg gaggagcggc cgggcctggg gccttgaggc      300
ccggggagag ccggggagcc gggcccgcgc gccgagatgt tgctgctgct gctactggcg      360
ccactcttcc tccgccccc gggcgcgggc ggggcgcaga cccccaacgc cacctcagaa       420
ggttgccaga tcatacaccc gccctgggaa ggggcatca ggtaccgggg cctgactcgg       480
gaccaggtga aggctatcaa cttcctgcca gtggactatg agattgagta tgtgtgccgg      540
ggggagcgcg aggtggtggg gcccaaggtc cgcaagtgcc tggccaacgg ctcctggaca      600
gatatggaca cacccagccg ctgtgtgaat cgaacgccac actcagaacg gcgcgcagtg      660
tacatcgggg cactgtttcc catgagcggg ggctggccag ggggccaggc ctgccagccc      720
gcggtggaga tggcgctgga ggacgtgaat agccgcaggg acatcctgcc ggactatgag      780
ctcaagctca tccaccacga cagcaagtgt gatccaggcc aagccaccaa gtacctatat      840
gagctgctct acaacgaccc tatcaagatc atccttatgc ctggctgcag ctctgtctcc      900
acgctggtgg ctgaggctgc taggatgtgg aacctcattg tgcttttccta tggctccagc    960
tcaccagccc tgtcaaaccg gcagcgtttc cccactttct tccgaacgca cccatcagcc     1020
acactccaca accctacccg cgtgaaactc tttgaaaagt ggggctggaa gaagattgct     1080
accatccagc agaccactga ggtcttcact tcgactctgg acgacctgga ggaacgagtg     1140
aaggaggctg gaattgagat tactttccgc cagagtttct tctcagatcc agctgtgccc     1200
gtcaaaaacc tgaagcgcca ggatgcccga atcatcgtgg actttttcta tgagactgaa     1260
gcccggaaag ttttttgtga ggtgtacaag gagcgtctct ttgggaagaa gtacgtctgg     1320
ttcctcattg ggtggtatgc tgacaattgg ttcaagatct acgacccttc tatcaactgc     1380
acagtggatg agatgactga ggcggtggag ggccacatca aactgagat tgtcatgctg      1440
aatcctgcca atacccgcag catttccaac atgacatccc aggaatttgt ggagaaacta     1500
accaagcgac tgaaaagaca ccctgaggag acaggaggct tccaggaggc accgctggcc     1560
tatgatgcca tctgggcctt ggcactggcc ctgaacaaga catctggagg aggcggccgt     1620
tctggtgtgc gcctggagga cttcaactac aacaaccaga ccattaccga ccaaatctac     1680
cgggcaatga actcttcgtc ctttgagggt gtctctggcc atgtggtgtt tgatgccagc     1740
ggctctcgga tggcatggac gcttatcgag cagcttcagg gtggcagcta caagaagatt     1800
ggctactatg acagcaccaa ggatgatctt tcctggtcca aaacagataa atggattgga     1860
gggtccccc cagctgacca gaccctggtc atcaagacat tccgcttcct gtcacagaaa      1920
ctctttatct ccgtctcagt tctctccagc ctgggcattg tcctagctgt tgtctgtctg     1980
tcctttaaca tctacaactc acatgtccgt tatatccaga actcacagcc caacctgaac     2040
aacctgactc tgtgggctg ctcactggct ttagctgctg tcttcccct ggggctcgat       2100
ggttaccaca ttgggaggaa ccagtttcct ttcgtctgcc aggcccgcct ctggctcctg     2160
ggcctgggct ttagtctggg ctacggttcc atgttcacca agatttggt ggtccacacg      2220
gtcttcacaa agaaggaaga aaagaaggag tggaggaaga ctctggaacc ctggaagctg     2280
tatgccacag tgggcctgct ggtgggcatg gatgtcctca ctctcgccat ctggcagatc     2340
gtggaccctc tgcaccggac cattgagaca tttgccaagg aggaacctaa ggaagatatt     2400
gacgtctcta ttctgccca gctggagcat tgcagctcca ggaagatgaa tacatggctt      2460
ggcattttct atggttacaa ggggctgctg ctgctgctgg gaatcttcct tgcttatgag     2520
accaagagtg tgtccactga gaagatcaat gatcaccggg ctgtgggcat ggctatctac     2580
aatgtggcag tcctgtgcct catcactgct cctgtcacca tgattctgtc cagccagcag    2640
```

```
-continued
gatgcagcct ttgcctttgc ctctcttgcc atagttttct cctcctatat cactcttgtt    2700
gtgctctttg tgcccaagat gcgcaggctg atcacccgag gggaatggca gtcggaggcg    2760
caggacacca tgaagacagg gtcatcgacc aacaacaacg aggaggagaa gtcccggctg    2820
ttggagaagg agaaccgtga actggaaaag atcattgctg agaaagagga gcgtgtctct    2880
gaactgcgcc atcaactcca gtctcggcag cagctccgct cccggcgcca cccaccgaca    2940
cccccagaac cctctggggg cctgcccagg ggacccoctg agcccoccga ccggcttagc    3000 tgtgatggga gtcgagtgca tttgctttat aagtgagggt agggtgaggg aggacaggcc    3060 agtagggga gggaaaggga gaggggaagg gcagggact caggaagcag ggggtccca     3120 tccccagctg ggaagaacat gctatccaat ctcatctctt gtaaatacat gtcccctgt    3180 gagttctggg ctgatttggg tctctcatac ctctgggaaa cagaccttt tctctcttac    3240 tgcttcatgt aattttgtat cacctcttca caatttagtt cgtacctggc ttgaagctgc    3300
tcactgctca cacgctgcct cctcagcagc ctcactgcat cttcctcttc ccatgcaaca    3360
ccctcttcta gttaccacgg caaccctgc agctcctctg cctttgtgct ctgttcctgt    3420
ccagcagggg tctcccaaca agtgctcttt ccaccccaaa ggggcctctc cttttctcca    3480
ctgtcataat ctctttccat cttacttgcc cttctatact ttctcacatg tggctccccc    3540
tgaattttgc ttcctttggg agctcattct tttcgccaag gctcacatgc tccttgcctc    3600
tgctctgtgc actcacgctc agcacacatg catcctcccc tctcctgcgt gtgcccactg    3660
aacatgctca tgtgtacaca cgcttttccc gtatgctttc ttcatgttca gtcacatgtg    3720
ctctcgggtg ccctgcattc acagctacgt gtgcccctct catggtcatg ggtctgccct    3780
tgagcgtgtt tgggtaggca tgtgcaattt gtctagcatg ctgagtcatg tctttcctat    3840
ttgcacacgt ccatgtttat ccatgtactt tccctgtgta ccctccatgt accttgtgta    3900 cttcttccc ttaaatcatg gtattcttct gacagagcca tatgtaccct accctgcaca    3960
ttgttatgca ctttccccca attcatgttt ggtggggcca tccacaccct ctccttgtca    4020
cagaatctcc atttctgctc agattccccc catctccatt gcattcatgt actaccctca    4080
gtctacactc acaatcatct tctcccaaga ctgctccctt ttgttttgtg ttttttttgag    4140 gggaattaag gaaaaataag tgggggcagg tttggagagc tgcttccagt ggatagttga    4200
tgagaatcct gaccaaagga aggcacccctt gactgttggg atagacagat ggacctatgg   4260
ggtgggaggt ggtgtccctt tcacactgtg gtgtctcttg gggaaggatc tccccgaatc   4320
tcaataaacc agtgaacagt gtgactcggc aaaaaaaaa a                         4361
```

In another embodiment, the B1 subunit is encoded by a nucleotide molecule that is a homologue of SEQ ID NOs: 4, 5, or 6. In another embodiment, the nucleotide molecule is a variant of SEQ ID NOs: 4, 5, or 6. In another embodiment, the nucleotide molecule is an isomer of SEQ ID NOs: 4, 5, or 6. In another embodiment, the nucleotide molecule is a fragment of SEQ ID NOs: 4, 5, or 6. In another embodiment, the nucleotide molecule comprises SEQ ID NOs: 4, 5, or 6. Each possibility represents a separate embodiment of the present invention.

The epitope recognized by an antibody detected by a method of the present invention is, in another embodiment, a conformational epitope. In another embodiment, the epitope is a linear epitope. In another embodiment, the epitope is any other type of epitope known in the art. Each possibility represents a separate embodiment of the present invention.

In one embodiment, ectopic expression of B1 subunit by nervous tissue contained in the teratomas contributes to break immune tolerance. In another embodiment, a combination of factors such as an adjuvant effect of the prodromal viral-like illness that occur in most subjects, and a genetic predisposition in certain embodiments, play additional roles in the initiation of the immune response tested for using the diagnosis methods described herein.

In one embodiment, a pathogenic role of B1 antibodies in paraneoplastic anti-$GABA_B$ encephalitis is shown by the correlation between patients' symptoms and antibody titers.

In another embodiment, the subject exhibits antibodies that react with an extracellular neuronal antigen. In another embodiment, the subject exhibits antibodies that react with an antigen exposed on the cell surface of a neuron. In another embodiment, patients with antibodies to extracellular antigens exhibit, under the conditions utilized herein, enhanced responsiveness to immune therapy.

In another embodiment, a method of the present invention utilizes, detects, or tests for a target antigen identified by a method disclosed herein. In another embodiment, the target antigen is identified by a library screening technique. In another embodiment, the target antigen is identified by cDNA library screening. In another embodiment, the target antigen is identified by reactivity with cultured neurons. In another embodiment, the target antigen is identified by immunoprecipitation by patient's antibodies. Each possibility represents a separate embodiment of the present invention.

In another embodiment, the present invention provides a method of diagnosing encephalitis in a subject, comprising the steps of obtaining a biological sample from said subject; and testing the biological sample for an antibody to the B1 subunit of a $GABA_B$ receptor, whereby the presence of said antibody in said biological sample indicates an autoimmune encephalitis, thereby determining a cause of an encephalitis in a subject.

In another embodiment, the present invention provides a method of diagnosing a tumor associated with an autoimmune encephalitis in a subject, comprising the steps of: obtaining a biological sample from the subject; and testing the biological sample for an antibody to the B1 subunit of a $GABA_B$ receptor, whereby the presence of said antibody indicates the presence of an occult tumor in said subject and that said tumor is a cause of said autoimmune encephalitis.

In another embodiment, the present invention provides a method of diagnosing epilepsy in a subject, comprising the steps of: obtaining a biological sample from the subject; and testing the biological sample for the presence of an antibody to the B1 subunit of a $GABA_B$ receptor, whereby the presence of said antibody indicates the presence of a tumor in said subject and said tumor is a cause of said epilepsy, thereby diagnosing epilepsy in a subject.

In another embodiment, the present invention provides a method of diagnosing a tumor in a subject having an epilepsy, comprising the step of: obtaining a biological sample from the subject; and testing the biological sample for the presence of an antibody to the B1 subunit of a $GABA_B$ receptor, whereby the presence of said antibody indicates the presence of a tumor in said subject, thereby diagnosing a tumor in a subject having an epilepsy.

In another embodiment, the present invention provides a method of treating autoimmune encephalitis in a subject, comprising the steps of: detecting a tumor associated with an autoimmune encephalitis by testing a body fluid from the subject for an antibody to the B1 subunit of a $GABA_B$ receptor, whereby a presence of said antibody indicates a presence of said tumor in said subject and that said tumor is a cause of said autoimmune encephalitis; and treating said tumor. In another embodiment, the tumor is treated within four months of the onset of a symptom associated with autoimmune encephalitis.

Methods for testing a reactivity of a body fluid against neuronal antigens are well known in the art. In one embodiment, enzyme-linked immunoabsorption assay (ELISA) is used to test for the presence of an antibody. In another embodiment, immunocytochemistry is used to test for the presence of an antibody. In another embodiment, immunoprecipitation is used to test for the presence of an antibody. In another embodiment, one of the methods enumerated herein is utilized. In another embodiment, neuronal tissue is fixed with PFA. In another embodiment, any other method known in the art is utilized. Each possibility represents a separate embodiment of the present invention.

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

Methods and kits for detection of antibodies are well known in the art, and are described, for example, in Ances BM et al (Treatment-responsive limbic encephalitis identified by neuropil antibodies: MRI and PET correlates. Brain 2005; 128:1764-1777) and Vitaliani et al (Paraneoplastic encephalitis, psychiatric symptoms, and hypoventilation in ovarian teratoma. Ann Neurol 2005; 58:594-604.). Each possibility represents a separate embodiment of the present invention.

Methods for diagnosing limbic encephalitis (LE) are well known in the art. In another embodiment, patients with LE develop subacute confusion, irritability, depression, sleep disturbances, seizures, short-term memory loss, and/or dementia. In another embodiment, the pathological substrate of LE is an inflammatory disorder that predominantly involves the limbic system (hippocampi, amygdala, and cingulate gyms). In another embodiment, biopsy and autopsy studies demonstrate interstitial and perivascular infiltrates of T cells, and less frequently B cells, along with microglial activation, neuronal degeneration, and/or gliosis. In another embodiment, inflammatory infiltrates are found in areas distant from the limbic system. In another embodiment, the infiltrates remain mild and clinically silent. In another embodiment, the infiltrates become prominent and develop into a disorder called encephalomyelitis. Additional methods of diagnosing LE are described, for example, in Gultekin SH et al (Paraneoplastic limbic encephalitis: neurological symptoms, immunological findings and tumour association in 50 patients. Brain 2000;123:1481-1494). Each possibility represents a separate embodiment of the present invention.

In another embodiment, an antigen of the present invention is homologous to a peptide disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID NO: 1-6 of greater than 70%. In another embodiment, "homology" refers to identity to a sequence selected from SEQ ID NO: 1-6 of greater than 72%. In another embodiment, "homology" refers to identity to one of SEQ ID NO: 1-6 of greater than 75%. In another embodiment, "homology" refers to identity to a sequence selected from SEQ ID NO: 1-6 of greater than 78%. In another embodiment, "homology" refers to identity to one of SEQ ID NO: 1-6 of greater than 80%. In another embodiment, "homology" refers to identity to one of SEQ ID NO: 1-6 of greater than 82%. In another embodiment, "homology" refers to identity to a sequence selected from SEQ ID NO: 1-6 of greater than 83%. In another embodiment, "homology" refers to identity to one of SEQ ID NO: 1-6 of greater than 85%. In another embodiment, "homology" refers to identity to one of SEQ ID NO: 1-6 of greater than 87%. In another embodiment, "homology" refers to identity to a sequence selected from SEQ ID NO: 1-6 of greater than 88%. In another embodiment, "homology" refers to identity to one of SEQ ID NO: 1-6 of greater than 90%. In another embodiment, "homology" refers to identity to one of SEQ ID NO: 1-6 of greater than 92%. In another embodiment, "homology" refers to identity to a sequence selected from SEQ ID NO: 1-6 of greater than 93%. In another embodiment, "homology" refers to identity to one of SEQ ID NO: 1-6 of greater than 95%. In another embodiment, "homology" refers to identity to a sequence selected from SEQ ID NO: 1-6 of greater than 96%. In another embodiment, "homology" refers to identity to one of SEQ ID NO: 1-6 of greater than 97%. In another embodiment, "homology" refers to identity to one of SEQ ID NO: 1-6 of greater than 98%. In another embodiment, "homology" refers to identity to one of SEQ ID NO: 1-6 of greater than 99%. In another embodiment, "homology" refers to identity to one of SEQ ID NO: 1-6 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7. 6), 5× Denhardt's solution, 10% dextran sulfate, and 20 µg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen PE, Curr Opin Struct Biol 9:353-57; and Raz NK et al Biochem Biophys Res Commun 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

EXAMPLES

Example 1

The $GABA_B$ Rece s for is a Novel Autoantigen of Severe Limbic Encephalitis with Prominent Seizures Materials and Methods Patients and Controls. The inventors of the instant application studied 410 patients for encephalitis suspected to be paraneoplastic or immune mediated against neuronal cell surface antigens. Antibodies were identified in 357: 275 had antibodies to the NR1 subunit of the NMDAR, 27 voltage-gated potassium channels (VGKC), 19 glutamic acid decarboxylase (GAD), 15 G1uR1/2 subunits of the AMPAR, 11 Ma2, 8 HuD, and 2 against CRMP5. Of the remaining 53 patients, 15 had serum or CSF antibodies against neuronal cell surface antigens predominantly visible in the neuropil of rat brain, all showing a similar immunostaining. These features and the dramatic response to treatment of the index case (patient # 1) focused the current study in these 15 patients. Information was obtained by the authors or provided by referring physicians. CSF or serum from 104 patients, including 91 randomly selected from the above and 13 with GAD-antibody associated syndromes served as controls.

Animal tissue, antibodies, and immunohistochemistry on rat brain. Female Wistar rats were euthanized and the brain was removed, sagittally sectioned, immersed in 4% paraformaldehyde at 4° C. for 2 hours, cryoprotected with 40% sucrose for 24 hours, and snap frozen in chilled isopentane.

Immunohistochemistry on rat brain and human tissue. Paraffin-embedded tissue was deparaffinized and the antigens retrieved. Seven-micrometer-thick frozen (or 4 p.m paraffin) tissue sections were serially incubated with 0.3% $H_2O_2$ for 20 minutes, 10% goat serum for 1 hour, and patient or control serum (1:250), CSF (1:10), or a guinea pig polyclonal antibody against an intracellular epitope of the $GABA_B$ receptor (1:200; invitrogen, Carlsbad, Calif.) at 4° C. overnight. After using the appropriate secondary antibodies (all 1:2,000), reactivities were developed with the avidin-biotin-peroxidase method. Results were photographed under a fluorescence microscope using Zeiss Axiovision software (Zeiss, Thornwood, N.Y.).

Immunohistochemistry with human tissue (SCLC tumors) utilized IgG purified from patients' sera and labeled with biotin. In these studies no secondary antibody was needed, avoiding background caused by irrelevant human IgG present in the tissue.

Immunohistochemistry on frozen sections of rat brain was performed with patients' or control serum (1:250), CSF (1:10), or $GABA_{B1}$ antibody using a standard avidin-biotin peroxidase method, or double immunolabeling with patients' serum or CSF and the $GABA_{B1}$ antibody, followed by the appropriate Alexa Fluor secondary antibodies.

Immunocytochemistry on neuronal cultures and HEK293 cells. Rat hippocampal neuronal cultures were prepared. Live neurons grown on coverslips were incubated for 1 hour at 37° C. with patient or control serum (final dilution 1:200) or CST (1:10). After removing the media and extensive washing with phosphate-buffered saline (PBS), neurons were fixed with 4% paraformaldehyde, permeabilized with 0.1% Triton X-100, and single or double immunolabeled with a guinea pig polyclonal $GABA_{B1}$ receptor antibody (1:200), followed by the corresponding Alexa Fluor secondary antibodies diluted 1:2,000 (Molecular Probes, Eugene, Oreg.). Results were photographed under a fluorescence microscope using Zeiss Axiovision software (Zeiss, Thornwood, N.Y.).

HEK293 cells were transfected with plasmids containing rodent $GABA_{B1}$ or $GABA_{B2}$ subunits of the $GABA_B$ receptor or plasmids without insert (control), using a method previously reported. In other experiments, cells were cotransfected with $GABA_{B1}$ and $GABA_{B2}$ in equimolar ratios. Cells were grown for 24 hours after transfection before assessment. Transfected cells were fixed in 4% paraformaldehyde, permeabilized with 0.1% Triton X-100 and then incubated with patients' serum (1:200) or CSF (100%) and the indicated guinea pig polyclonal $GABA_{B1}$ receptor antibody (1:20,000) or a polyclonal $GABA_{B2}$ receptor antibody (1:10,000, generated by Dr. Moss) overnight at 4° C., washed in PBS, and incubated with the appropriate Alexa Fluor secondary antibodies (1:2,000; Molecular Probes). Results were photographed under a fluorescence microscope using Zeiss Axiovision software (Zeiss, Thornwood, N.Y.).

Antibody titers were determined using HEK293 cells expressing $GABA_{B1/B2}$ incubated with serial dilutions of serum and CSF, starting at ½ dilution.

Patients' antibody IgG subtypes were determined in serum or CSF using the indicated HEK293 transfected cells, and secondary anti-human antibodies against IgG1, IgG2, IgG3, and IgG4 (all diluted 1:200; Sigma, St. Louis, MO) as reported.

Immunoprecipitation and immunoblot. Live neurons obtained as above, were grown in 100mm wells (density $10^6$ neurons/well), and incubated at 37° C. with filtered patient serum (diluted 1:500) for 1 hour. Neurons were then washed with PBS, lysed with buffer (NaCl 150 mM, EDTA 1mM, tris(hydroxymethyl)aminomethane [Tris]-HCl 100 mM, deoxycholate acid 0.5%, 1% Triton X-100 [Sigma Labs, St. Louis, Mo.], pH 7.5) containing protease inhibitors (P8340; Sigma Labs), and centrifuged at $16.1 \times 10^3$ g for 20 minutes at 4° C. The supernatant was retained and incubated with protein A/G agarose beads (20423; Pierce, Rockford, Ill.) overnight at 4° C., centrifuged, and the pellet containing the beads with patients' antibodies bound to the target cell surface antigen was then washed with PBS, aliquoted, and kept at −80° C. An aliquot of this pellet was resuspended in Laemmli buffer, boiled for 10 minutes, separated in a 4 to 15% sodium dodecyl sulfate polyacrylamide gel electrophoresis, and the proteins visualized with EZBlue gel staining (G1041; Sigma Labs). Distinctive protein bands precipitated by patient serum were excised from the gel and analyzed using mass spectrometry at the proteomic facility at the University of Pennsylvania. After characterization of the antigen, frozen aliquots of the indicated pellets were separated in a sodium dodecyl sulfate polyacrylamide gel electrophoresis as described earlier, transferred to nitrocellulose (162-0115; Bio-Rad, Hercules, Calif.), and blotted with the indicated polyclonal antibodies against $GABA_B$' (1:2000) or $GABA_{B2}$ (1:1000) receptor subunits. The reactivity was developed using the appropriate biotinylated secondary antibodies (1:2000) and the avidin-biotin peroxidase, diaminobenzidine method.

Quantitative analysis of $GABA_B$ receptor clusters using confocal microscopy. Fourteen to 21-day in vitro (div) live rat hippocampal neurons were incubated with patient CSF (1:30 dilution in Neuro-Basal B27 medium; GIBCO, Carlsbad, Calif.) for 24 hours, washed, fixed in paraformaldehyde (4% paraformaldehyde, 4% sucrose in PBS) for 5 minutes, permeabilized with 0.25% Triton X-100 for 10 minutes, and blocked with 5% normal goat serum for 1 hour. Neurons were then incubated with a guinea pig polyclonal antibody against an intracellular epitope of the $GABA_B$ receptor (1:1000; Invitrogen) and a mouse monoclonal antibody against the presynaptic marker Bassoon (1:200; Stressgen, Victoria, British Columbia, Canada), washed, and incubated with the appropriate fluorescent-conjugated secondary antibodies (1:1000, Molecular Probes).

Images were obtained using a laser-scanning confocal microscope (Leica TCS SP2; Leica, Deerfield, Ill.). For each image, laser light levels and detector gain and offset were adjusted so that no pixel values were saturated. Images of labeled neurons were stored digitally for subsequent analysis. Images were thresholded, areas of interest containing dendrites were selected, and the number of individual clusters along neuronal dendrites was determined using interactive software (ImageJ; Research Services Branch, National Institute of Mental Health, Bethesda, MD). The co-localization of clusters labeled with patient's antibodies, commercial $GABA_B$ antibodies and the synaptic marker Bassoon was quantified using a software Macro implemented in ImageJ.

Results

Figure 1B:
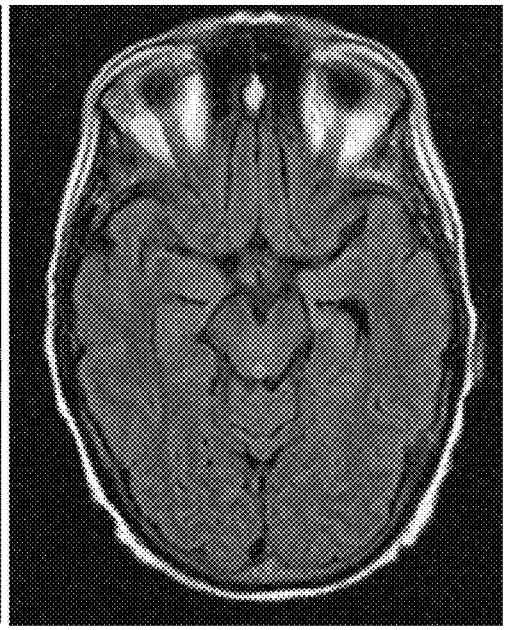
Figure 1C:
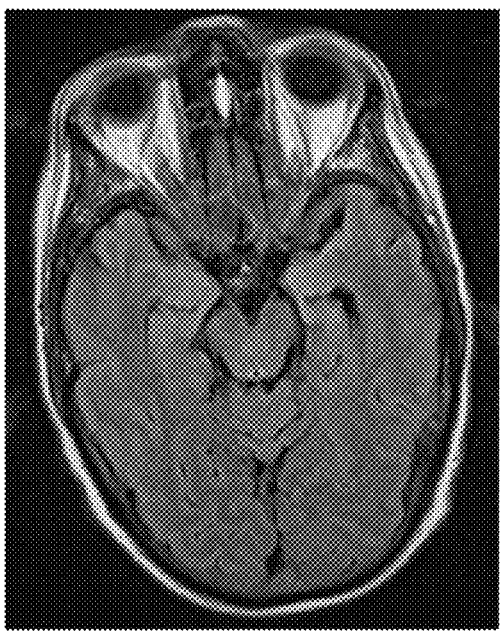
Figure 1D:

Index Patient (Case #1 in tables): A 60-year-old woman was hospitalized for confusion, memory problems, and new onset generalized tonic-clonic and partial complex seizures refractory to treatment. At examination, she was disoriented to place and time, and had extremely poor concentration and short-term memory. Aside from saccadic pursuits with lateral gaze, no cranial nerve abnormalities were noted. Strength, sensation, reflexes, and coordination were normal. MRI of the brain revealed bilateral medial temporal lobe fluid-attenuated inversion recovery (FLAIR) increased signal compatible with limbic encephalitis (FIG. 1a). EEGs showed diffuse slowing and bilateral periodic lateralized epileptiform discharges (PLEDS). CSF demonstrated 9 white blood cells (WBC)/µl, total protein concentration 35 mg/dL, glucose 71 mg/dL, and negative oligoclonal bands and cytology. PCR for herpes simplex virus, West Nile virus, and St. Louis encephalitis were negative. Hyponatremia (119 mEq/L) due to syndrome of inappropriate anti-diuretic hormone (SIADH) secretion was noted. Serum and CSF analysis of paraneoplastic antibodies was negative. Combined CT and fluorodeoxyglucose (FDG)-PET revealed mediastinal lymphadenopathy, proven by biopsy to be small-cell lung cancer (SCLC). The patient was treated with antiepileptics (levetiracetam, valproic acid, phenytoin) and immunotherapy (intravenous immunoglobulins [IVIg], corticosteroids), immediately followed by chemotherapy with cisplatin and etoposide. There was a rapid and dramatic improvement of short term memory and cognition, and the seizures completely resolved. After completion of these treatments the patient received standard prophylactic whole brain radiation therapy. Repeat brain MRI one month after symptom presentation showed improvement of the abnormal FLAIR signal (FIG. 1b); subsequent MRIs 3- and 9-months later were unchanged except for progressive general atrophy, likely secondary to radiation (FIG. 1c, d). One year after symptom presentation, the patient had only mild memory and cognitive deficits and lived independently.

Figure 3A:
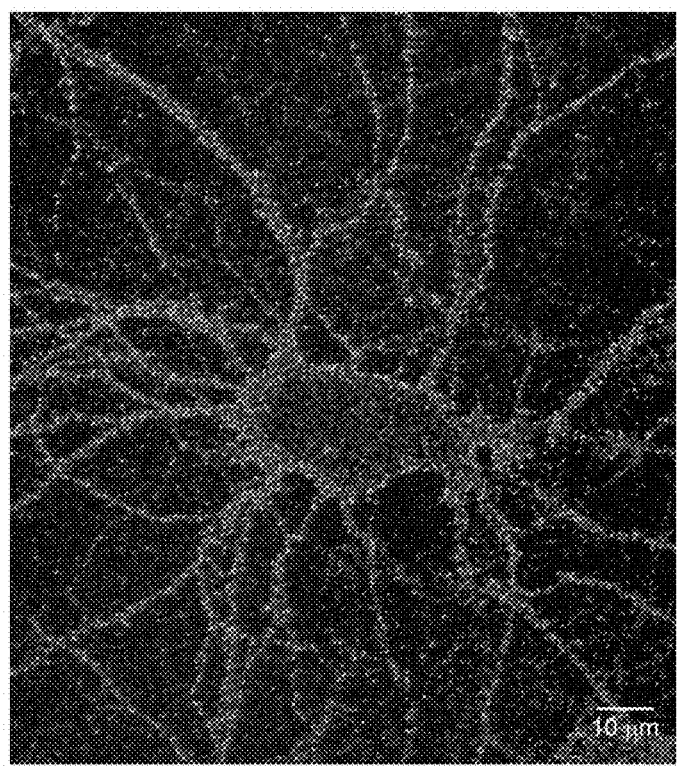
FIG. 3 shows that patients antibodies react with extracellular epitopes and precipitate the B1 and B2 subunits of the $GABA_B$ receptor. Culture of rat hipppocampal neurons were incubated (live, non-permeabilized) with the CSF of a patient with LE. The intense dot-like reactivity indicates patient's antibodies with cell surface antigens (A); scale bar =10 μm. The precipitation of these antigens using patient's antibodies is shown in a gel in which proteins are visualized with EZBlue (B). Patient's antibodies (P) precipitated two protein bands at ~105-90 kDa; these bands are not seen in the precipitate using CSF from a control individual (N). Sequencing of all bands using mass spectrometry demonstrated the B1 and B2 subunits of the $GAB$ $A_B$ receptor. Other smaller bands were proteolytic fragments and patient's IgG. Subsequent transfer of the gel to nitrocellulose and immunoblotting with monoclonal antibodies specific for each of the $GABA_B$ subunits confirmed that patient's antibodies precipitated the B1 and B2 subunits (Panels in C).

Detection of antibodies against a novel neuronal cell surface autoantigen. Analysis of serum and CSF of the index case and 14 additional patients from the indicated selection of cases showed reactivity with the neuropil of rat brain (FIG. 2), in a pattern different from that reported with the NR1 subunit of the NMDAR, G1uR1/2 subunits of the AMPAR, or VGKC antibodies. To determine whether the antibodies reacted with extracellular epitopes, non-fixed and non-permeabilized cultures of rat hippocampal neurons were incubated with patients' serum or CSF, showing intense reactivity with the cell surface (FIG. 3a).

Figure 3B:
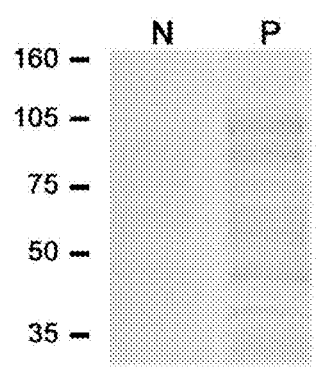
Figure 3C:
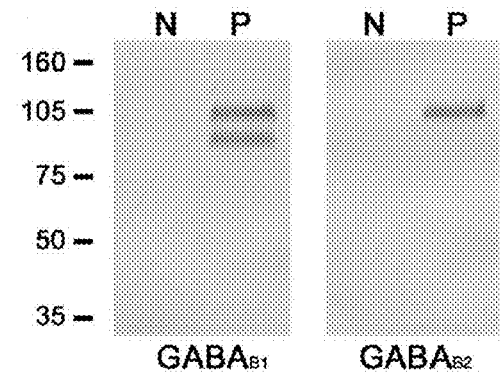
Figure 5A:
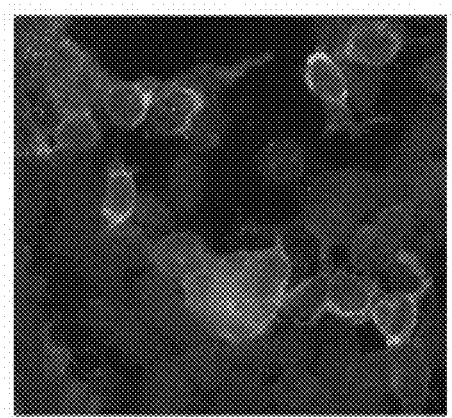
FIG. 5 shows the detection of antibodies to the $GABA_{B1}$ subunit using a HEK293 cell based assay. HEK293 cells transfected with B1 and B2 subunits of the $GABA_B$ receptor show reactivity with CSF from a patient with limbic encephalitis (A) and a polyclonal antibody against the B1 subunit of the $GABA_B$ receptor (B); both reactivities are merged in (C). The same cells do not react with CSF from a control individual (D, E); reactivities merged in (F). Immunofluorescent method; x400.
Figure 5B:
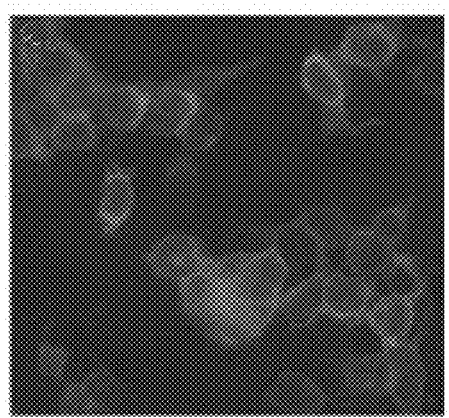
Figure 5C:
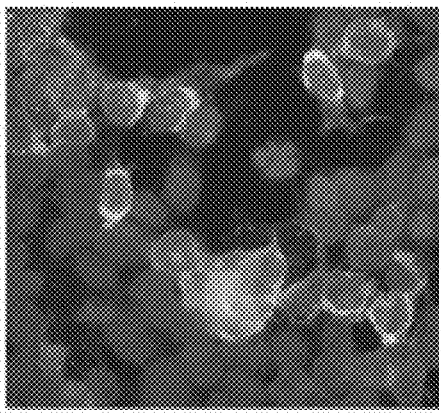
Figure 5D:
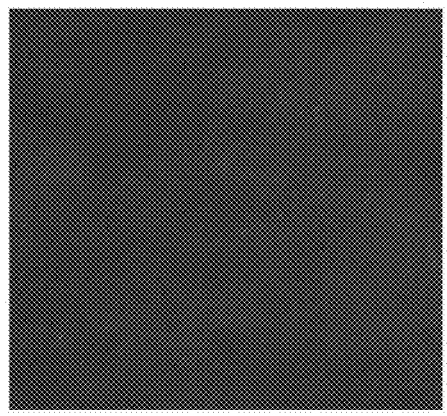
Figure 5E:
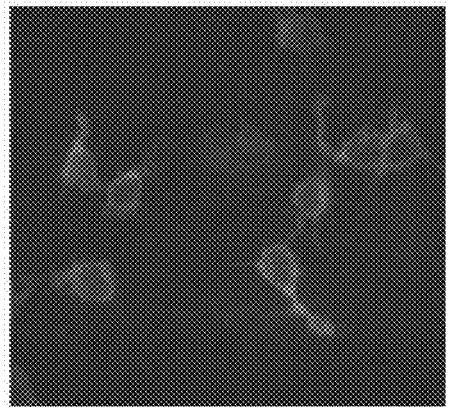
Figure 5F:
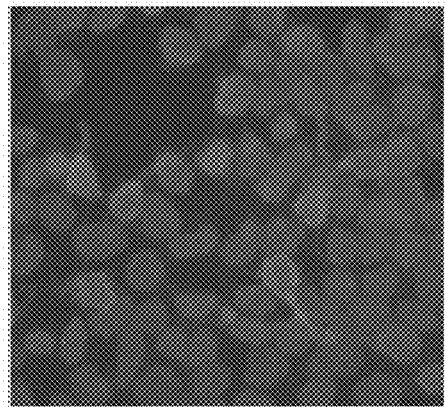

The neuronal cell surface antigen is the metabotropic $GABA_B$ receptor. To identify the cell surface antigen, live rat hippocampal neurons were incubated with patients' antibodies and the target antigen was immunoprecipitated. These studies produced two protein bands of approximately 105 and 90 kDa (FIG. 3b) that were analyzed by mass spectrometry demonstrating sequences derived from the B1 subunit of the metabotropic $GABA_B$ receptor. Because the $GABA_B$ receptor is a heterodimer composed of two subunits, B1 and B2, both with a similar molecular weight, the inventors next examined by immunoblot and polyclonal antibodies specific for each subunit to determine whether patients' antibodies had precipitated both subunits. These studies confirmed that patient antibodies co-precipitated B1 and B2 subunits of the $GABA_B$ receptor (FIG. 3c).

The specificity of patient antibodies for $GABA_B$ receptors was determined by triple immunolabeling of cultured neurons (patient antibodies; a guinea pig polyclonal antibody to a non-competing intracellular $GABA_{B1}$ receptor epitope; and a pre-synaptic marker [Bassoon]), and the degree of co-localization quantified by confocal microscopy, as reported (FIG. 4). The binding of antibodies to $GABA_B$ receptor clusters was analyzed on the dendrites of 24 neurons on 4 separate coverslips. This showed that 103±0.8% of patient antibody-labeled $GABA_B$ receptor clusters co-localized with clusters labeled by the guinea pig polyclonal $GABA_B$ receptor antibody, and 107±0.7% of guinea pig antibody-labeled clusters co-localized with those labeled by patient antibodies (numbers slightly higher than 100% occur due to overlapping of a few clusters labeled by patient antibodies with two guinea pig antibody-labeled clusters and vice-versa). These results indicate that essentially all patient's anti-neuronal cell surface antibodies target the $GABA_B$ receptors and that virtually all neuronal $GABA_B$ receptors are labeled by patient's antibodies.

To determine which of the two $GABA_B$ receptor subunits contained the target epitope, HEK293 cells were transfected with $GABA_{B1}$, $GABA_{B2}$, or both receptor subunits and immunocytochemically tested with patients' antibodies. All 15 patients had serum or CSF antibodies that specifically reacted with the $GABA_{B1}$ receptor subunit (FIG. 5), and one had additional reactivity with the $GABA_{B2}$ subunit. These findings indicate that HEK293 cells expressing $GABA_{B1,B2}$ or $GABA_{B1}$ receptor subunits provide a substrate for an unambiguous diagnostic test. Similar studies with the 104 control cases showed that two patients, both with syndromes attributed to GAD autoimmunity, had $GABA_{B1}$ receptor antibodies at low titers (CSF 1:2, serum negative), not visible with brain immunohistochemistry.

Analysis of antibody IgG subtypes was performed in serum or CSF of 6 randomly selected patients. All had IgG1 $GABA_{B1}$ antibodies; two had additional IgG3, and one IgG2 antibodies.

Neurological symptoms. Demographic information, clinical features, treatment, and outcome are shown in Tables 1 and 2. Among the 15 patients with high titer $GABA_{B1}$ receptor antibodies and limbic encephalitis (cases #1-15), the median age was 62 years (range, 24-75); 8 were men. Thirteen patients presented with subacute onset of seizures, confusion, and severe memory impairment, and in two (#3 and 13) the memory deficit and confusion preceded the seizures by a few weeks. Most seizures had a temporal lobe onset with secondary generalization, and three patients had status epilepticus. Ten patients had uni- or bilateral medial temporal lobe FLAIR/T2 increased signal consistent with limbic encephalitis, I had a small area of increased FLAIR signal in the corpus callosum, and 4 had normal brain MR1. The CSF was abnormal in 9 of 10 patients for whom data was available. The most common abnormality was lymphocytic pleocytosis in 8 patients. EEG studies were available from 12 patients; 9 showed temporal lobe seizures, epileptiform discharges, or temporal lobe slowing; 2 had generalized slowing and 1 was normal. Several types of seizures were noted on EEG, including complex partial seizures (often of temporal lobe onset), status epilepticus, and subclinical seizures.

The two control cases with low titer of $GABA_{B1}$ antibodies (cases #16 and 17 in Tables 1 and 2) developed different syndromes in association with high titer GAD antibodies in serum and CSF. Neither of these 2 patients developed seizures or limbic dysfunction. One had progressive cerebellar ataxia, and the other gait instability, muscle stiffness, rigidity, myoclonus, and dysarthria, categorized as encephalomyelitis with rigidity.

TABLE 1

Demographic Features and symptoms

| Case No. | Sex/Age (yr) | Tumor | Presenting Symptoms | Other clinical-immunological features |
|---|---|---|---|---|
| 08-299 | F/60 | SCLC | Subacute onset of complex partial seizures, confusion, memory impairment | SIADH |
| 06-165 | M/66 | SCLC | Subacute onset of seizures, confusion, memory deficit, behavioral problems | N-type VGCC antibodies |
| 06-235 | F/53 | SCLC | Rapidly progressive memory deficits, abnormal sleeping habits, followed by frequent seizures (focal, secondarily generalized), confusion, decline in mental status leading to coma | Pruritic rash with initial weakness. |

TABLE 1-continued

Demographic Features and symptoms

| Case No. | Sex/Age (yr) | Tumor | Presenting Symptoms | Other clinical-immunological features |
|---|---|---|---|---|
| 08-017 | M/75 | Mediastinal adenopathy | Subacute onset of seizures, psychosis, encephalitis. Rapidly progressed to death before definitive diagnosis or treatment. | Poor respiratory status, refused intubation |
| 08-152 | M/68 | Neuroendocrine tumor of the lung | Subacute onset of seizures, status epilepticus, confusion | — |
| 08-623 | F/43 | CT and FDG/PET negative | Subacute onset of secondarily generalized tonic-clonic seizures, bizarre behaviors, delusions, paranoia, memory impairment. | N-type VGCC antibodies |
| 09-086 | M/69 | CT and FDG/PET negative | Subacute onset of right temporal lobe seizures, status epilepticus, severe encephalopathy, severe memory deficit, confusion | Prior history of bipolar disorder |
| 07-305 | F/24 | CT and FDG/PET negative | Subacute onset of seizures, status epilepticus, confusion, fever. Required intubation and ventilation due to poor level of consciousness and airway protection | N-type VGCC antibodies |
| 06-026 | M/63 | CT and FDG/PET negative | Subacute onset of seizures, memory deficit, paranoia, psychosis, gustatory hallucinations | TPO and GAD antibodies; hypothyroidism and type 2 diabetes mellitus |
| 08-278 | F/45 | Benign ovarian mass | Subacute onset of complex partial an generalized seizures and short-term memory deficits | — |
| 09-176 | F/62 | CT chest, abdomen, pelvis negative | Subacute onset generalized seizures, confusion, decreased level of consciousness, fluent aphasia, abnormal orolingual movements. | — |
| 07-004 | M/29 | None | Subacute onset of left temporal lobe epilepsy; generalized tonic-clonic refractory seizures. No cognitive deterioration. | Childhood seizures |
| 09-083 | F/30 | CT and FDG/PET negative | 3 month history of severe memory deficit, followed by seizures (generalized, subclinical) | GAD antibodies without endocrinopathy |
| 01-696 Graus | M/69 | SCLC | Subacute onset of generalized tonic-clonic seizures, worsened short-term memory deficit | Mild short-term memory deficit from past history of subarachnoid hemorrhage |
| 07-1051 Graus | M/70 | SCLC | Subacute onset of seizures (partial motor and generalized). Severe short-term memory loss, confabulation, visual hallucinations, disorientation, agitation | GAD, TPO, and SOX1 antibodies. No endocrinopathy |
| 08-114 | F/63 | CT and FDG/PET negative | 1 year progression of cerebellar ataxia. Normal mental status, no seizures, no muscle spasms or stiffness | GAD antibodies, adult onset insulin dependent diabetes mellitus |
| 08-398 | F/61 | CT and FDG/PET negative | 6 week history of gait disturbance, lower extremity myoclonus and stiffness; dysphagia, dysarthria, nystagmus, left gaze palsy. No seizures or cognitive symptoms | GAD, TPO and thyroglobulin antibodies (mild thyroid dysfunction) |

SCLC: small cell lung cancer; FDG/PET: Fluoro-deoxyglucose/positron emission tomography; SIADH: syndrome of inappropriate anti-diuretic hormone; GAD: glutamic-acid decarboxylase; TPO: thyroid peroxidase; VGCC: voltage-gated calcium channels.

TABLE 2

Diagnostic tests, treatment and outcome.

| Case No. | MRI | CSF | Serum CSF titers | Chronological list of treatments | Outcome (duration of follow-up) |
|---|---|---|---|---|---|
| 08-299 | FLAIR/T2 increased signal in medial temporal lobes | 9 WBC/μL; protein 35; no OCBs | S, 1:640 CSF, 1:160 | IVIg, corticosteroids, chemotherapy | Substantial improvement. Mild residual short term memory deficit. Lives independently. Seizure free (12 months) |

TABLE 2-continued

Diagnostic tests, treatment and outcome.

| Case No. | MRI | CSF | Serum CSF titers | Chronological list of treatments | Outcome (duration of follow-up) |
|---|---|---|---|---|---|
| 06-165 | Normal | Normal | S, 1:1280 CSF, n/a | Corticosteroids, IVIg, chemotherapy | Substantial improvement. Died of metastatic disease (15 months) |
| 06-235 | FLAIR/T2 increased signal in medial temporal lobes | n/a | S, 1:160 CSF, n/a | Tumor removal (lobectomy) IVIg | Partial improvement after tumor removal and IVIg (4 months); lost to follow-up. |
| 08-017 | Normal | n/a | S, 1:2560 CSF, 1:640 | None | Died soon after presentation of rapidly progressive respiratory failure |
| 08-152 | FLAIR/T2 increased signal in medial temporal lobes | n/a | S, 1:1280 CSF, n/a | Supportive | Died 6 months after symptom presentation. $GABA_B$ antibodies detected after patient's death in archived serum |
| 08-623 | FLAIR/T2 increased signal in small area of corpus callosum | 95 WBC/μL; protein 104; increased IgG index | S, n/a CSF, 1:640 | Corticosteroids, mycophenylate mofetil | Substantial improvement. Lives independently. Seizure free (9 months) |
| 09-086 | FLAIR/T2 increased signal in left mesial temporal lobe | n/a | S, n/a CSF, 1:640 | Corticosteroids, plasma exchange | Initial substantial response to corticosteroids. Relapsed 1 month later. Died after 5 months in ICU with refractory seizures, status epilepticus, and systemic complications. |
| 07-305 | FLAIR/T2 increased signal in medial temporal lobes | 19 WBC/μL; protein 46 | S, 1:5120 CSF, 1:2560 | Corticosteroids, plasma exchange | Substantial improvement. Mild residual short-term memory deficit. Seizures free (3 months) |
| 06-026 | FLAIR/T2 increased signal in medial temporal lobes | 75 WBC/μL; protein 26; +OCBs | S, negative CSF, 1:4 | Corticosteroids | Full recovery (41 months) |
| 08-278 | FLAIR/T2 increased signal in medial temporal lobes | 81 WBC, protein 30 | S, 10,240 CSF, n/a | Corticosteroids | Substantial improvement. Residual short-term memory deficit. Lives independently. Seizure free (72 months) |
| 09-176 | Normal | 20 WBC/μL; protein 22 | S, 1:40 CSF, 1:40 | Corticosteroids | Full recovery (6 months) |
| 07-004 | FLAIR/T2 increased signal in left medial temporal lobe and insula | 950 WBC/μL; +OCB | S, negative CSF, 1:10 | Symptomatic | Temporal lobe biopsy 20 months after symptom presentation showing reactive astrocytosis, without inflammation. No follow-up available after biopsy. |
| 09-083 | FLAIR/T2 increased signal in medial temporal lobes | 4 WBC/μL; protein 109; 6 OCBs | S, negative CSF, 1:4 | Corticosteroids | Full recovery, except for infrequent brief episodes of visual hallucinations (10 months) |
| 01-696 Graus | FLAIR/T2 increased signal in left medial temporal lobe | Traumatic; negative cytology. | | Chemotherapy | Residual short-term memory deficit; seizures controlled; died of sepsis (3 months) |
| 07-1051 Graus | Normal | 0 WBC/μL; protein 95 | S, n/a CSF, 1:640 | IVIg, corticosteroids, chemotherapy | Seizures responded to antiepileptics; memory deficit persisted; died of cancer-related treatment (2 months) |
| 08-114 | Normal | 3 WBC/μL; protein 78; 1 OCB | S, negative CSF, 1:2 | IVIg | No seizures or cognitive deficits. Limited response of cerebellar ataxia to IVIg (12 months) |
| 08-398 | Normal | 2 WBC/μL; Protein 52; +OCBs | S, negative CSF, 1:2 | IVIg, corticosteroids | No seizures or cognitive deficits. Full recovery after steroids and IVIg (12 months) |

WBC: white blood cells (normal <4 μl), FLAIR: fluid-attenuated inversion recovery; n/a: not available; IVIg: intravenous immunoglobulin. ICU: intensive care unit.

Other autoantibodies. In addition to $GABA_B$ antibodies, 6 of 15 patients (40%) had antibodies to one or more of the following: 3 GAD, 2 thyroid peroxidase (TPO), 3 N-type VGCC, and 1 SOX1 antibodies. Only 1 of the 3 patients with GAD antibodies had endocrinopathy, and 1 of the 3 patients with VGCC antibodies had a SCLC. The patient with SOX1 antibodies had a SCLC.

Associated Tumors. Seven patients had a lung nodule or mediastinal adenopathy, with pathological confirmation of SCLC or neuroendocine tumor in 6. In all instances the tumor was detected at the time of neurological symptom presentation. Since most lung tumors were diagnosed by needle biopsy, no tissue was available for analysis of $GABA_B$ receptor expression. Yet, 3 of 4 SCLCs from control cases (without antibodies or encephalitis) showed reactivity with a guinea pig polyclonal antibody to $GABA_{B1}$ receptor and patients' biotinylated IgG suggesting that these receptors are expressed by SCLC.

Treatment and Outcome. Nine patients (60%) had substantial neurological response to immunotherapy or treatment of the tumor. The median follow-up of these patients is 10 months (3-72); 1 subsequently died of tumor progression (15 months) and 1 was lost to follow-up (4 months). Six patients did not show sustained neurological improvement; three (#4, 14, 15 in Tables 1 and 2) died soon after presentation of the disorder as a result of tumor or chemotherapy-related complications, and the other three were diagnosed with $GABA_B$ receptor antibodies after death (#5 and 7) or were lost to follow-up (#12). In the latter three cases an autoimmune process was only considered in patient #7 who received corticosteroids and plasma exchange; the other two patients did not receive immunotherapy. Overall, excluding the two patients that were lost to follow-up, neurological improvement correlated with prompt tumor control or immunotherapy (Fisher's exact test =0.003).

The inventors of the instant application have discovered a new form of autoimmune encephalitis that associates with antibodies to extracellular epitotes of the $GABA_B$ receptor and is potentially treatment-responsive. Based on clinical, MRI, and EEG findings, the brain regions most affected are the hippocampi and temporal lobes. Therefore it is not surprising that the resulting syndrome is indistinguishable from other types of limbic encephalitis, although some clinical and immunological features may suggest $GABA_B$ receptor autoimmunity. A notable finding is the development of prominent and severe seizures in all patients, representing the main reason for medical attention or hospital admission. Two frequently associated features are the identification of a lung cancer, and the concurrent presence of autoantibodies against antigens of unclear significance with the limbic syndrome. In contrast, pharmacological or genetic disruption of $GABA_B$ receptors result in phenotypes that closely resemble the limbic syndrome of patients with $GABA_B$ receptor antibodies. Moreover, in humans, a common $GABA_B$ receptor polymorphism associates with temporal lobe epilepsy.

Forty seven percent of patients with encephalitis and $GABA_B$ receptor antibodies had a lung nodule or mediastinal adenopathy which pathological, radiological and demographic features (age range 53-75 years, all smokers) were consistent with a SCLC or neuroendocrine tumor. Therefore, $GABA_B$ autoimmunity is likely involved in a number of patients with limbic encephalitis and SCLC previously considered "without antibodies" or attributed to antibodies to intracellular antigens, particular if a dramatic (and unexpected) improvement occurred after treatment of the tumor or immunotherapy. Moreover, anti-$GABA_B$ receptor encephalitis can occur without cancer association. Five of such patients were young (median age 30 years, range 24-45), without history of smoking, negative comprehensive cancer screening including CT/FDG-PET, and in some cases a long-term follow-up (41 and 72 months), making unlikely the presence of an occult cancer in all cases. In this respect, anti-$GABA_B$ receptor encephalitis is similar to other synaptic autoimmunities of the central (NMDAR, AMPAR) or peripheral nervous system (acetylcholine receptor, P/Q-type VGCC) that may occur with or without cancer association. As occur in these disorders, 40% of patients with anti-$GABA_B$ receptor encephalitis (50% of those without tumor) had additional autoantibodies, indicating a propensity to autoimmunity. The most interesting immunological overlap was with antibodies to GAD (an intracellular antigen), bringing into consideration that a subset of patients with limbic encephalitis attributed to GAD autoimmunity may have antibodies to extracellular epitopes of the $GABA_B$ receptor as a plausible cause of the symptoms. All together, antibodies to the $GABA_{B1}$ receptor can be used to diagnose encephalitis, usually manifesting as a limbic syndrome, but with early and prominent seizures. By the time antibodies are determined the serum titers can be very low, and examining both serum and CSF is preferred. Identification of these antibodies should prompt the search for a SCLC, although approximately 50% of patients do not have cancer. Treatment of the tumor and immunotherapy with corticosteroids, IVIg, or plasma exchange often results in improvement. The dramatic and specific antibody binding to $GABA_B$ receptor in live neurons and the similarity with experimental phenotypes in which the function of the receptor is abrogated shows the antibodies are pathogenic.

Example 2

$GABA_B$ Receptor Antibodies in Limbic Encephalitis and Anti-GAD-Associated Neurological Disorders We analyzed the frequency of $GABA_BR$-ab in 147 patients with LE or neurological syndromes associated with GAD-ab. We examined the presence of $GABA_BR$-ab in 70 LE patients (33 paraneoplastic with onconeural antibodies, 18 paraneoplastic without onconeural antibodies, and 19 idiopathic with either GAD-abor seronegative), and 77 patients with GAD-ab-associated neurological syndromes other than LE (29 stiff- person syndrome (SPS), 28 cerebellar ataxia, 14 epilepsy, and 6 with diverse paraneoplastic neurological syndromes). $GABA_BR$-ab were analyzed in stored samples of serum or CSF by indirect immunofluorescence on HEK293 cells transfected with $GABA_{B1}$ and $GABA_{B2}$ receptor subunits.

$GABA_BR$-ab were detected in 10 of the 70 LE patients (14%). Eight had SCLC and two were idiopathic. One of the eight LE patients with SCLC had an additional onconeural antibody (Hu) and two GAD-ab. $GABA_BR$-ab were identified in 7 (70%) of the 10 patients with LE and SCLC without onconeural antibodies. $GABA_BR$-ab antibodies were not found in patients with GAD-ab and SPS, cerebellar ataxia or epilepsy. However, one patient with GAD-ab and cerebellar ataxia also presented $GABA_BR$-ab in the setting of an anaplastic carcinoid of the thymus.

Our results show that $GABA_BR$-ab are the most common antibodies found in LE associated with SCLC previously considered "seronegative". In patients with GAD-ab, the frequency of $GABA_BR$-ab is low and only observed in the context of cancer.

Methods

Patients. We reviewed all patients with final diagnosis of LE, or with other neurological syndromes associated with GAD-ab whose serum or CSF was sent to our laboratory (Barcelona, Spain) for analysis of antineuronal antibodies. LE was defined by the subacute onset of short-term memory loss, behavior change, seizures, and involvement of the temporal lobes by EEG, imaging studies, or postmortem examination. LE was considered definite paraneoplastic if a tumor was diagnosed or the serum presented well characterized onconeural antibodies (Hu, Yo, Ri, CV2, Ma2, amphiphysin). The diagnosis of definite idiopathic LE required the absence of cancer and well characterized onconeural antibodies, and a follow-up of at least three years. LE patients with a shorter follow-up were classified as possible idiopathic LE. Patients with GAD-ab were classified, as previously reported, in one of the following groups: stiff-person syndrome (SPS), cerebellar ataxia, isolated epilepsy, and paraneoplastic neurological syndromes. The information was obtained from forms filled out by the referring neurologists, telephone interviews, and review of the clinical records. The study was approved by the Ethic Committee of the Hospital Clinic.

Immunological studies. Onconeural antibodies, SOX1-ab, and GAD-ab were screened by immunohistochemistry performed on frozen sections of paraformaldehyde-perfused rat cerebellum using an avidin-biotin immunoperoxidase technique and confirmed by immunoblot when indicated. GAD-ab were confirmed by radioimmunoassay. Neuropil antibodies were screened by immunohistochemistry on frozen sections of rat brain post-fixed with 4% paraformaldehyde. The presence of AMPA glutamate receptor antibodies was confirmed by immunofluorescence on HEK-293 cells transfected with plasmids containing the appropriate antigens, and voltage-gated potassium channel (VGKC) antibodies were confirmed by radioimmunoassay.

$GABA_BR$-ab were screened on HEK293 cells transfected with plasmids containing rodent $GABA_{B1}$ and $GABA_{B2}$ in equimolar ratios. Positives samples were also analyzed by immunocytochemistry of rat hippocampal neuronal cultures. Both techniques have previously been described. Briefly, HEK293 transfected cells were incubated with the patients' serum (dilution 1:20) or CSF (1:2) for 1 h at 37° C., washed, fixed with 4% paraformaldehyde, incubated with a rabbit polyclonal $GABA_{B1}$ antibody (1:1000) (Santa Cruz Biotechnology, sc-14006; Santa Cruz, Calif.) followed by the appropriate Alexa Fluor secondary antibodies (Molecular Probes, Eugene, Oreg.). For immunocytochemistry of rat hippocampal neuronal cultures, live neurons grown on coverslips were incubated with the patients' serum (1:100) or CSF (1:2) for 1 h at 37° C., washed, fixed with 4% paraformaldehyde, and immunoreacted with anti-human IgG Alexa Fluor secondary antibody. Results were photographed under a fluorescence microscope using Zeiss Axiovision software (Zeiss, Thornwood, N.Y.). To confirm the specificity of the neuronal reactivity, all positive samples were pre-absorbed with the non neuronal cell line HEK293 to remove antibodies that could react with non neuronal specific surface antigens.

Results

Figure 7A:
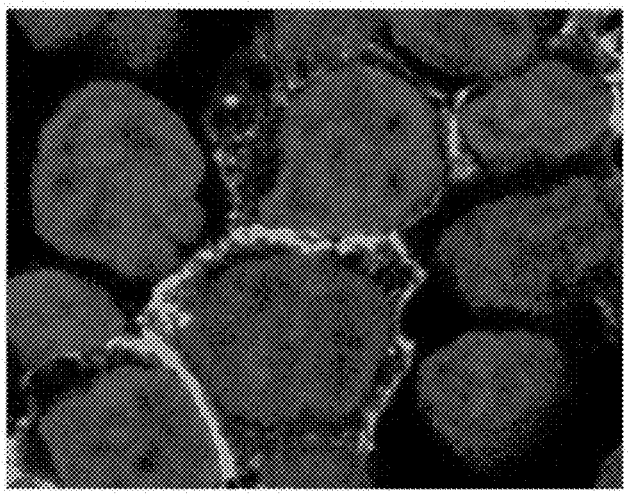
FIG. 7 shows detection of $GABA_B$R-ab using a HEK293 cell based assay. HEK293 cells were transfected to express $GABA_{B1/B2}$ receptor and incubated live, not permeabilized, with a patient's CSF. Afterwards, cells were fixed and incubated with a polyclonal antibody against an intracellular epitope of the B1 subunit of the $GABA_B$ receptor. Note that patient's CSF stains the cell surface of cells that specifically express $GABA_B$ receptors (A), as demonstrated by the intracellular reporter antibody (B). Both reactivities are shown merged in C. Nuclei counterstained with DAPI. Scale bar=20 μm.
Figure 7B:
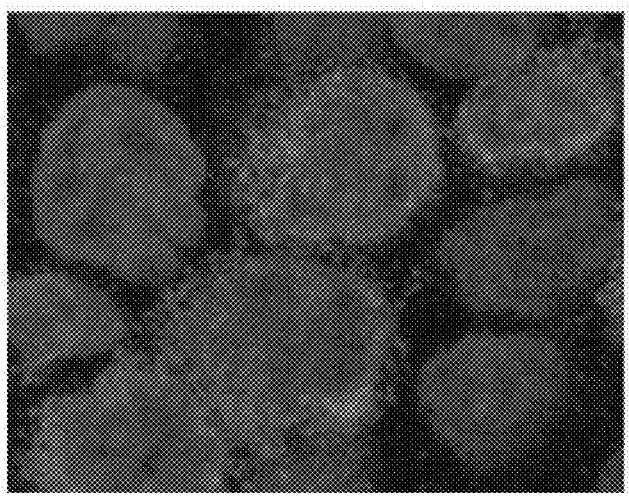
Figure 7C:
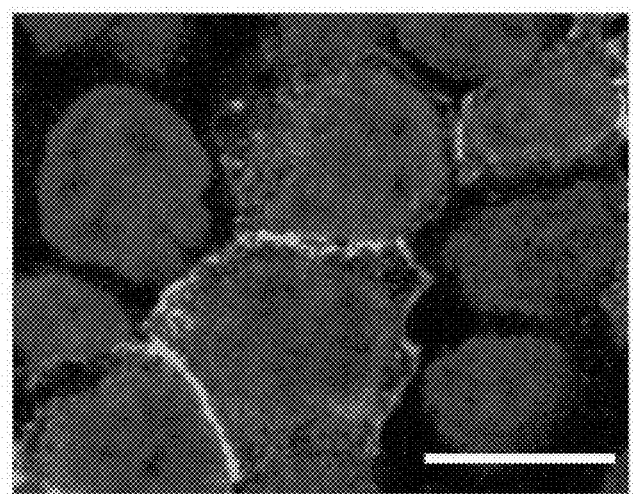
Figure 8:
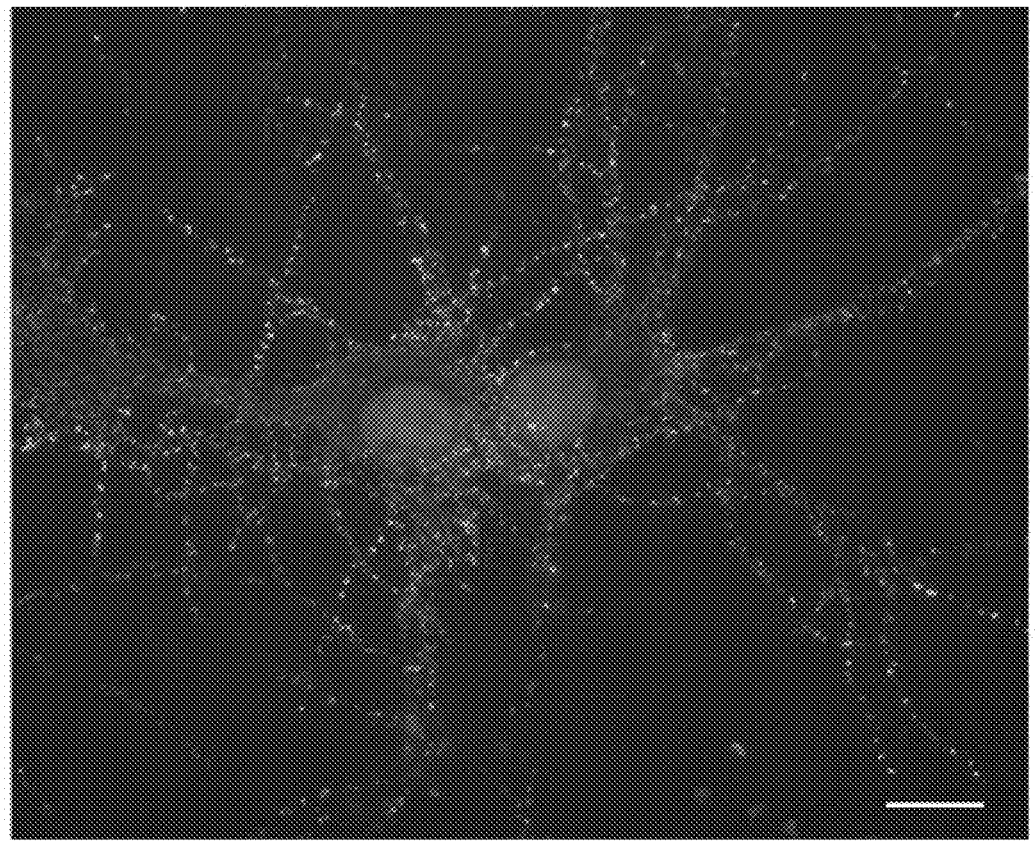
FIG. 8 shows Primary culture of rat hippocampal neurons incubated in vivo with CSF of a patient with $GABA_B$R-ab. There is an intense punctate reactivity in the neuronal membrane. Scale bar=20 μm.

Eleven patients tested positive for $GABA_BR$-ab on the screening of HEK293 cells transfected with the B1 and B2 subunits of the $GABA_BR$ (FIG. 7). All positive samples immunoreacted in vivo with primary cultures of hippocampal neurons (FIG. 8). $GABA_BR$-ab were positive in both serum and CSF in the 5 patients from whom paired samples were available. Median titer of $GABA_BR$-ab was 1/120 (range 40-2000) in serum and 1/60 (range 20-640) in the CSF.

We found $GABA_BR$-ab in 10 patients with LE. Positive $GABA_BR$-ab were identified more frequently in the group of paraneoplastic LE without onconeural antibodies (previously considered "seronegative") (Table 3). Seven (39%) of the 18 patients were $GABA_BR$-ab-positive and all had SCLC. In total, positive $GABA_BR$-ab were identified in 7 (70%) of the 10 patients with LE and SCLC without onconeural antibodies. The other three patients were positive for AMPAR-ab. The coincidence of $GABA_BR$-ab and GAD-ab occurred in 2 patients with SCLC whereas the other three patients with LE and GAD-ab associated with other tumors (thymoma 2, lymphoma) and were $GABA_BR$-ab-negative.

In this study, we analyzed 33 patients with LE and onconeural antibodies, and only one, with Hu-ab and SCLC, tested positive for $GABA_BR$-ab. However, 4 of the 7 LE patients with $GABA_BR$-ab without onconeural antibodies presented antibodies against intracellular antigens (Table 4). Two patients had GAD-ab (one also SOX1-ab), one Hu-ab, and, in two cases previously reported, one had brain serine/threonine kinase (BRSK)2-ab and the other SOX1 and VGKC-ab.

No tumor was identified in the remaining 2 $GABA_BR$-ab-positive patients but the follow-up is too short to classify them as definite idiopathic LE. None of the 5 patients with idiopathic LE and GAD-ab were positive for $GABA_BR$-ab (Table 3).

A summary of the clinical features of the $GABA_BR$-ab-positive patients is presented in Table 4. Nine of the 10 patients with GAB $A_BR$-ab and LE were men. Median age was 60 years (range.47-70 years). Seizures were the predominant and presenting symptom in 8 patients and 2 required admission to the intensive care unit for control of the seizures. All patients also presented confusion, disorientation, memory loss, or behavior changes consistent with encephalitis predominantly involving the limbic system. The CSF disclosed mild lymphocyte pleocytosis in 4 patients. Brain MRI showed increased fluid-attenuated inversion recovery signal in one or both hippocampus and amygdala in 7 patients. In 4 of them the initial brain MRI was reported normal. Only 1 patient had hyponatremia. Seven patients were treated with steroids, intravenous immunoglobulins or combination of both drugs. Three of the 8 patients with SCLC were also treated with chemotherapy. Only 2 patients made a complete recovery (one without cancer) and none of them had concurrent antineuronal antibodies. Partial responses to the indicated treatments were achieved in 4 with a relapse in one of them.

$GABA_BR$-ab were not detected in 71 patients with GAD-ab and SPS, cerebellar ataxia or epilepsy. In contrast, one of the 6 patients with paraneoplastic neurological syndromes and GAD-ab was $GABA_BR$-ab positive (Table 3). She was a 57 year-old woman with a known anaplastic carcinoid of the thymus and bone metastases. She developed nausea, vomiting, gait instability and diplopia. Neurological examination disclosed a normal mental status, bilateral horizontal nystagmus, and cerebellar gait ataxia. The patient was treated with oral steroids and the symptoms slowly resolved over the ensuing three months.

TABLE 3

Frequency of $GABA_BR$-ab in 147 patients with limbic encephalitis or GAD-ab-associated neurological syndromes

| Syndrome | Number of sera (CSF) | $GABA_BR$-ab positive (%) | Comments on positive cases |
|---|---|---|---|
| Paraneoplastic LE | 51 (21) | 8 (16) | |
| With onconeural-ab[1] | 33 (14) | 1 (3) | Hu-ab with SCLC |
| Without onconeural-ab[2] | 18 (7) | 7 (39) | All SCLC, GAD-ab: 2 |
| Idiopathic LE[3] | 19 (15) | 2 (14) | Short follow-up |
| GAD-ab-positive, non-LE | 77 (48) | 1 (1) | |
| Stiff-person syndrome | 29 (16) | 0 (0) | |
| Cerebellar ataxia | 28 (19) | 0 (0) | |
| Epilepsy | 14 (9) | 0 (0) | |
| Paraneoplastic | 6 (4) | 1 (17) | Cerebellar ataxia |

[1]Hu-ab (26), Ma2-ab (4), amphiphysin-ab (3). Lung cancer in 18 patients
[2]GAD-ab in five patients. Lung cancer in 11 patients (SCLC: 10; NSCLC: 1)
[3]GAD-ab in five patients. Definite idiopathic LE: 7 patients
SCLC: small cell lung carcinoma; LE: limbic encephalitis

TABLE 4

Clinical features and outcome of patients with positive GABA$_B$R antibodies

| Case | Age/sex | Cancer | Presenting symptoms[c] | MRI temporal lesions | CSF pleocytosis (WBC) | Other antineuronal-ab | Treatment | Outcome (months) |
|---|---|---|---|---|---|---|---|---|
| 1 | 60/M | SCLC | Status epilepticus | Left | Yes (unknown) | None | Steroids, IVIg | Partial control of seizures (dead from ICU complications) |
| 2 | 57/F | SCLC | Seizures, behavior change | Bilateral | No | None | Steroids, IVIg | Complete recovery[d] |
| 3 | 66/M | SCLC | Seizures, confusion | Normal | Yes (18) | GAD | Steroids, IVIg | Not available (short f-up) |
| 4[a] | 47/M | SCLC | Seizures, behavior change, memory impairment | Bilateral | Yes (20) | SOX1, VGKC | Steroids, IVIg, chemotherapy | Partial recovery, relapsing course (dead from cancer progression) |
| 5[b] | 69/M | SCLC | Seizures, memory impairment, confusion | Left | Traumatic | None | Chemotherapy | Partial response. Dead from cancer-related treatment(3 months) |
| 6[b] | 70/M | SCLC | Seizures, memory impairment, confusion | Normal | No | GAD, SOX1 | Steroids, IVIg, chemotherapy | No response. Dead from cancer-related treatment(2 months) |
| 7 | 58/M | SCLC | Seizures, memory impairment | Bilateral | Yes (15) | Hu | Steroids, IVIg, chemotherapy | No response (dead from LE) |
| 8[a] | 61/M | SCLC | Memory impairment | Bilateral | No | BRSK2 | None | No response. Lost when tumor was diagnosed 9 months later |
| 9 | 61/M | No | Confusion, seizures, behavior change | Normal | No | None | IVIg | Partial improvement. Severe ICU neuropathy |
| 10 | 50/M | No | Seizures, behavior and memory impairment | Bilateral | No | None | Antiepileptics only | Complete recovery |
| 11 | 57/F | Carcinoid of thymus | Subacute cerebellar ataxia | Normal | No | GAD | Steroids | Complete recovery |

SCLC: small cell lung cancer; WBC: white blood cells; BRSK2: Brain serine/threonine kinase 2.
[a]patients previously reported in references 10 and 9;
[b]included in the initial series of GABAR-ab (reference 4);
[c]predominant symptom listed first;
[d]Recovery before the start of chemotherapy.

To see if GABA$_B$R-ab associate with other cases of paraneoplastic cerebellar degeneration (PCD), we analyzed the serum or CSF of a series of 45 patients with PCD and lung cancer (35 with SCLC). The majority (73%) were included in a previous study. These patients had Hu-ab (15%) or voltage-gated calcium channel antibodies (50%). However, all were negative for GABA$_B$R-ab.

We found that GABA$_B$R-ab are the most common antibodies identified in patients with SCLC and LE previously considered "seronegative". Although the occurrence of GABA$_B$R-ab and GAD-ab was observed in an initial series of 15 patients, when we tested a larger series of patients with several types of neurological syndromes associated with GAD-ab, GABA$_B$R-ab were only identified in those who had a paraneoplastic syndrome.

At the time of the initial description of Hu-ab as markers of neurological syndromes associated with SCLC, we observed that up to 50% of patients with LE were "seronegative". The syndrome of these patients was highly restricted to the limbic system and seemed to improve more often after treatment of the cancer than that of patients with Hu-ab. In the current study, 7 of 10 (70%) patients with LE and SCLC had GABA$_B$R-ab. The other 3 patients were positive for AMPAR-ab. Taken together, all patients with LE and SCLC previously considered seronegative for classical paraneoplastic (onconeural) antibodies had antibodies against synaptic receptors.

In the current study we show that Hu-ab and GABA$_B$R-ab only occurred in 1 of 33 patients, suggesting that this specific association is uncommon. In contrast, we confirm that 40% of these patients had antibodies that are markers of the underlying SCLC (SOX1, BRSK2) or directed against VGKC or GAD.

In this study, all patients with concurrent GABA$_B$R-ab and GAD-ab had a paraneoplastic disorder. In the initial series, 2 of the 8 patients with idiopathic LE encephalitis had additional GAD-ab. We did not find GABA$_B$R-ab in patients with LE or isolated epilepsy with GAD-ab except in the two patients with SCLC. Our five patients with idiopathic LE and GAD-ab were women with a median age of 29 years and four presented with seizures. To determine how often both antibodies coincide in patients with idiopathic LE, we suggest routinely looking for GABA$_B$R-ab in all patients with LE suspected to be related with GAD-ab.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for diagnosing an encephalitis in a subject, comprising the steps of: obtaining a biological sample from said subject; and testing said biological sample to determine the presence of an antibody to a GABA$_B$ receptor, whereby the presence of said antibody in said biological sample indicates an autoimmune encephalitis, wherein said antibody binds to the B1 subunit of said GABA$_B$ receptor, wherein the step of testing comprises an immunoassay to detect said antibody by an antigen, and wherein said antigen comprises the B1 subunit of said GABA$_B$ receptor, thereby determining a cause of an encephalitis in said subject.

2. The method of claim 1, whereby said antibody binds to the B2 subunit of said GABA$_B$ receptor.

3. The method of claim 1, whereby said autoimmune encephalitis is a paraneoplastic autoimmune encephalitis.

4. The method of claim 1, whereby the autoimmune encephalitis is anti-GABA$_B$ receptor encephalitis.

5. The method of claim 1, whereby said autoimmune encephalitis is a non-paraneoplastic, autoimmune encephalitis.

6. The method of claim 1, whereby said autoimmune encephalitis comprises a limbic encephalitis.

7. The method of claim 1, whereby said autoimmune encephalitis is associated with pathological symptoms.

8. The method of claim 7, whereby the symptoms are seizures; psychiatric symptoms; abnormality in cognition and behavior; a movement disorder or abnormal movements; a decreased level of consciousness; hypoventilation; amnesia or a memory deficit; or a combination thereof.

9. The method of claim 1, whereby said autoimmune encephalitis is associated with a tumor.

10. The method of claim 9, whereby said tumor is a small cell lung cancer or a neuroendocrine tumor of the lung or other organs.

11. The method of claim 1, whereby the biological sample is a cerebrospinal fluid (CSF).

12. The method of claim 1, whereby the biological sample is a serum or plasma.

13. A method for determining an increased likelihood of the presence an occult tumor associated with an autoimmune encephalitis in a subject, comprising the steps of: obtaining a biological sample from said subject; and testing said biological sample to determine the presence of an antibody to a GABA$_B$ receptor, whereby the presence of said antibody in said biological sample indicates the increased likelihood of the presence of said occult tumor in said subject and that said tumor is a cause of said autoimmune encephalitis, wherein said antibody binds to the B1 subunit of said GABA$_B$ receptor, wherein the step of testing comprises an immunoassay to detect said antibody by an antigen, and wherein said antigen comprises the B1 subunit of said GABA$_B$ receptor.

14. The method of claim 13, whereby said autoimmune encephalitis is a paraneoplastic autoimmune encephalitis.

15. The method of claim 13, whereby said autoimmune encephalitis comprises a limbic encephalitis.

16. The method of claim 13, whereby said autoimmune encephalitis is associated with seizures.

17. The method of claim 13, whereby said autoimmune encephalitis is associated with pathological symptoms.

18. The method of claim 17, whereby said pathological symptoms are psychiatric symptoms; an abnormality in cognition and behavior: a movement disorder; a decreased level of consciousness; hypoventilation; amnesia or a memory deficit; or a combination thereof.

19. The method of claim 13, whereby the body fluid is cerebrospinal fluid (CSF).

20. The method of claim 13, whereby the body fluid is a serum or plasma.

21. A method for diagnosing an epilepsy in a subject, comprising the steps of: obtaining a biological sample from said subject; and testing said biological sample to determine the presence of an antibody to a $GABA_B$ receptor, whereby the presence of said antibody in said biological sample indicates an increased likelihood of the presence of a tumor in said subject and said tumor is a cause of said epilepsy, wherein said antibody binds to the B1 subunit of said $GABA_B$ receptor, wherein the step of testing comprises an immunoassay to detect said antibody by an antigen, and wherein said antigen comprises the B1 subunit of said $GABA_B$ receptor, thereby diagnosing said epilepsy in said subject.

22. The method of claim 21, whereby the body fluid is cerebrospinal (CSF) fluid.

23. The method of claim 21, whereby the body fluid is a serum or plasma.

24. The method of claim 21, whereby said $GABA_B$ receptor-associated encephalitis is anti-$GABA_B$ receptor encephalitis.

25. The method of claim 21, whereby said autoimmune encephalitis is a non-paraneoplastic, autoimmune encephalitis.

26. A method for determining an increased likelihood of the presence a tumor in a subject having an epilepsy, comprising the step of: obtaining a biological sample from said subject; and testing said biological sample to determine the presence of an antibody to a $GABA_B$ receptor, whereby the presence of said antibody in said biological sample indicates the increased likelihood of the presence of a tumor in said subject, wherein said antibody binds to the B1 subunit of said $GABA_B$ receptor, wherein the step of testing comprises an immunoassay to detect said antibody by an antigen, and wherein said antigen comprises the B1 subunit of said $GABA_B$ receptor, thereby diagnosing said tumor in said subject having said epilepsy.

27. A method for treating an autoimmune encephalitis in a subject, comprising the steps of: determining an increased likelihood of the presence a tumor associated with said autoimmune encephalitis by testing a body fluid from said subject for an antibody to a $GABA_B$ receptor, whereby the presence of said antibody in said body fluid indicates the increased likelihood of the presence of said tumor in said subject and that said tumor is a cause of said autoimmune encephalitis, wherein said antibody binds to the B1 subunit of said $GABA_B$ receptor; and treating said tumor based on the determination of the increased likelihood of the presence of said tumor.

28. The method of claim 27, whereby said encephalitis is associated with occult tumor.

29. The method of claim 27, whereby said tumor is a small cell lung cancer or a neuroendocrine tumor of the lung or other organs.

30. The method of claim 27, wherein the tumor is treated within four months of the onset of a symptom associated with autoimmune encephalitis.

31. The method of claim 27, whereby the step of treating said tumor comprises removing said tumor in combination with immunotherapy or chemotherapy.

32. The method of claim 27, whereby said antibody binds to the B2 subunit of said $GABA_B$ receptor.

33. The method of claim 27, whereby said autoimmune encephalitis is a $GABA_B$ receptor-associated encephalitis.

34. The method of claim 27, whereby said autoimmune encephalitis is a paraneoplastic autoimmune encephalitis.

35. The method of claim 27, whereby said autoimmune encephalitis comprises a limbic encephalitis.

36. The method of claim 27, whereby said autoimmune encephalitis is associated with pathological symptoms.

37. The method of claim 36, whereby the symptoms are seizures; psychiatric symptoms; abnormality in cognition and behavior; a movement disorder or abnormal movements; a decreased level of consciousness; hypoventilation; amnesia or a memory deficit; or a combination thereof.

38. A method of treating autoimmune encephalitis in a subject, comprising the steps of: determining an increased likelihood of the presence a tumor associated with said autoimmune encephalitis by testing a body fluid from said subject for an antibody to a $GABA_B$ receptor, whereby the presence of said antibody in said body fluid indicates the increased likelihood of the presence of said tumor in said subject and that said tumor is a cause of said autoimmune encephalitis, wherein said antibody binds to the B1 subunit of said $GABA_B$ receptor; and treating said tumor within four months of the onset of a symptom associated with autoimmune encephalitis based on the determination of the increased likelihood of the presence of said tumor.

39. The method of claim 38, whereby said encephalitis is associated with occult tumor.

40. The method of claim 38, whereby said antibody binds to the B2 subunit of said $GABA_B$ receptor.

41. The method of claim 38 or 40, wherein said subunit is a monomer of a multimer.

42. The method of claim 41, wherein said multimer is a receptor homomer.

43. The method of claim 42, wherein said homomer is a homo-dimer that comprises two B1 subunits.

44. The method of claim 41, wherein said multimer is a receptor heteromer.

45. The method of claim 44, wherein said heteromer comprises a B1 subunit and a B2 subunit.

46. The method of claim 44, wherein said heteromer comprises a B1-a subunit and a B2 subunit.

47. The method of claim 44, wherein said heteromorphy comprises a B1-b subunit and a B2 subunit.

48. The method of claim 44, wherein said heteromer comprises a B1-c subunit and a B2 subunit.

* * * * *

UNITED STATES PATENT AND TRADEMARK OFFICE
CERTIFICATE OF CORRECTION

| | | |
|---|---|---|
| PATENT NO. | : 8,685,656 B2 | Page 1 of 1 |
| APPLICATION NO. | : 13/498355 | |
| DATED | : April 1, 2014 | |
| INVENTOR(S) | : Josep Dalmau | |

It is certified that error appears in the above-identified patent and that said Letters Patent is hereby corrected as shown below:

In the Specification

In column 1, line 3, the following paragraph should be inserted:

--GOVERNMENT INTEREST STATEMENT

This invention was made with government support under grant no. R01 CA107192 awarded by the National Institute of Health. The government has certain rights in the invention.--

Signed and Sealed this
Second Day of December, 2014

Michelle K. Lee
*Deputy Director of the United States Patent and Trademark Office*